(12) United States Patent
Shin et al.

(10) Patent No.: US 10,465,241 B2
(45) Date of Patent: Nov. 5, 2019

(54) HIGH RESOLUTION STR ANALYSIS USING NEXT GENERATION SEQUENCING

(71) Applicant: The Board of Trustees of the Leland Stanford Junior University, Stanford, CA (US)

(72) Inventors: Giwon Shin, Stanford, CA (US); Billy Tsz Cheong Lau, Palo Alto, CA (US); HoJoon Lee, Stanford, CA (US); Hanlee P. Ji, Stanford, CA (US)

(73) Assignee: THE BOARD OF TRUSTEES OF THE LELEAND STANFORD JUNIOR UNIVERSITY, Stanford, CA (US)

( * ) Notice: Subject to any disclaimer, the term of this patent is extended or adjusted under 35 U.S.C. 154(b) by 639 days.

(21) Appl. No.: 15/177,115

(22) Filed: Jun. 8, 2016

(65) Prior Publication Data
US 2016/0362751 A1    Dec. 15, 2016

Related U.S. Application Data

(60) Provisional application No. 62/175,985, filed on Jun. 15, 2015, provisional application No. 62/200,904, filed on Aug. 4, 2015.

(51) Int. Cl.
*C12Q 1/6869* (2018.01)

(52) U.S. Cl.
CPC .................. *C12Q 1/6869* (2013.01)

(58) Field of Classification Search
None
See application file for complete search history.

(56) References Cited

PUBLICATIONS

Anvar, et al. "TSSV: a tool for characterization of complex allelic variants in pure and mixed genomes", vol. 30 No. 12 2014, pp. 1651-1659.
Bornman, et al. "Short-read, high-throughput sequencing technology for STR genotyping", Biotech Rapid Dispatches. ; 2012: 1-6.
Cao, et al "Inferring short tandem repeat variation from paired-end short reads", Nucleic Acids Research, 2014, vol. 42, No. 3, e16, pp. 1-11.
Carlson, et al. "MIPSTR: a method for multiplex genotyping of germline and somatic STR variation across many individuals", Genome Research, 2015, 25:750-761.
(Continued)

*Primary Examiner* — Kaijiang Zhang
(74) *Attorney, Agent, or Firm* — James S. Keddie; Bozicevic, Field & Francis LLP

(57) ABSTRACT

A method for analyzing short tandem repeats (STRs) is described herein. In some embodiments, the method comprises: separately digesting two portions of a genomic sample at sites that are upstream and downstream of an STR; fragmenting those products; ligating adaptors to the fragmentation products; selectively amplifying part of the top strand but not the bottom strand of the ligation products derived from the first portion, and part of the bottom strand but not the top strand of the ligation products derived from the second portion; sequencing at least some of the amplification products to produce a plurality of top strand reads and a plurality of bottom strand reads; and counting the number of STR repeats in a sequence read. A kit for performing the method is also provided.

16 Claims, 20 Drawing Sheets

Specification includes a Sequence Listing.

(56) References Cited

PUBLICATIONS

Duitama, et al. "Large-scale analysis of tandem repeat variability in the human genome", 5728-5741 Nucleic Acids Research, 2014, vol. 42, No. 9.
Guilmatre, et al. "Rapid multiplexed genotyping of simple tandem repeats using capture and high-throughput sequencing", Hum Mutat. Sep. 2013 ; 34(9): 1304-1311.
Gymrek, et al. "lobSTR: a short tandem repeat profiler for personal genomes", Genome Research, 2012, 22:1154-1162.
Highnam, et al. "Accurate human microsatellite genotypes from high-throughput resequencing data using informed error profiles", Nucleic Acids Research, 2013, vol. 41, No. 1 e32.
Van Neste, et al. "Forensic massively parallel sequencing data analysis tool: Implementation of MyFLq as a standalone web- and Illumina BaseSpace1-application", Forensic Science International: Genetics 15 (2015) 2-7.
Van Neste, et al. "Forensic STR analysis using massive parallel sequencing", Forensic Science International: Genetics 6 (2012) 810-818.
Warshauer, et al. "STRait Razor: A length-based forensic STR allele-calling tool for use with second generation sequencing data", Forensic Science International: Genetics 7 (2013) 409-417.
Willems, et al. "The landscape of human STR variation", Genome Research, 2015, 24:1894-1904.

A

B

C

A

Reference Genome (hg19)

gRNA target

Probe

STR

Negative control

Pile-up

CRISPR/Cas9

Pile-up

HIGH RESOLUTION STR ANALYSIS USING NEXT GENERATION SEQUENCING

CROSS-REFERENCING

This patent application claims the benefit of provisional application Ser. Nos. 62/175,985 filed on Jun. 15, 2015, and 62/200,904 filed on Aug. 4, 2015, which applications are incorporated by reference herein.

GOVERNMENT SUPPORT

This invention was made with Government support under contract 2013-DN-BX-K010 awarded by the United States Department of Justice. The Government has certain rights in the invention.

BACKGROUND

Microsatellites, otherwise called STRs, have multiple alleles that are defined by variation in the number of motif unit repeats. Given their multi-allelic characteristics, they have greater heterozygosity than single nucleotide polymorphisms (SNPs). STR polymorphisms are the result of motif insertions or deletions (indels), arising from slippage errors during DNA replication or recombination events. The diversity of microsatellite alleles is attributable to STR mutation rates (10-2 events per generation) that are significantly higher than the mutation rate for SNPs which are reported to be 10-8 events per generation. Due to their multi-allelic characteristics, STR genotyping has proven useful for the genetic characterization of individual, subpopulations and populations. Moreover, genotyping with approximately 20 STRs can identify an individual with high confidence, enabling its universal application for genetic identification in forensics.

STR genotyping relies on multiplexed PCR amplification of microsatellite loci followed by analysis based on size discrimination with capillary electrophoresis (CE). Forensic genetics employs the CE-based method for nearly all cases of genetic identification. However, this approach has many limitations. First, CE genotyping assays are restricted to thirty STR amplicons or less because of the inherent challenges of multiplexing PCR reactions. Second, CE has low analytical throughput, typically in the tens of markers. Third, PCR amplification of microsatellites introduces indel artifacts, also known as "stutter", that can obscure true genotypes, particularly when alleles are close in size. Finally, current STR genotyping methods have difficulty resolving alleles in DNA mixtures that are composed of multiple individual genomes. In forensic genetic analysis, it is nearly impossible to distinguish a specific individual DNA sample amongst multiple contributors, particularly when a specific component exists at a low ratio.

Next generation sequencing (NGS) assays have been developed for the analysis of STRs. These include whole genome sequencing (WGS), targeted sequencing using bait-hybridization capture oligonucleotides and multiplexed amplicon sequencing methods that include molecular inversion probes. Regardless of the approach, current NGS methods for STR analysis have significant limitations. STRs' repetitive motifs complicate traditional alignment methods and lead to mapping errors. Sequence reads that span an entire STR locus are the most informative for accurate genotyping. However, many NGS approaches produce reads that truncate the STR sequence, resulting in ambiguous genotypes.

STR genotypes can be determined from WGS data. However, the read coverage of an intact STR locus varies greatly with the standard WGS coverage (e.g. 30× to 60×) and reduces the reads with intact microsatellites. Lower coverage translates into decreased sensitivity and specificity for detecting microsatellite genotypes. Consequently, accurate STR genotyping requires much higher sequencing coverage than is practical with WGS, particularly in cases of genetic mixtures composed of different genomic DNA samples in varying ratios.

Targeted sequencing can improve STR coverage but current methods have limitations. For example, targeting STRs with bait-hybridization enrichment requires randomly fragmented genomic DNA—this reduces the fraction of informative reads containing a complete microsatellite to less than 5%. Furthermore, enrichment for STR loci is complicated by repetitive sequences with potential off-target hybridization. Sequencing library amplification or PCR-dependent multiplexed amplicons lead to significant increase in stutter errors.

SUMMARY

A method for analyzing short tandem repeats (STRs) is described herein. In some embodiments, the method comprises: (a) separately digesting a first portion of a genomic sample at a defined site that is upstream of an STR and a second portion of the sample at a defined site that is downstream of the STR; (b) fragmenting the cleavage products; (c) ligating adaptors to the fragmentation products; (d) selectively amplifying: part of the top strand but not the bottom strand of the ligation products derived from the first portion of the genomic sample, and part of the bottom strand but not the top strand of the ligation products derived from the second portion of the genomic sample; (e) sequencing at least some of the amplification products to produce a plurality of top strand reads and a plurality of bottom strand reads; and (f) counting the number of STR repeats in a sequence read. This count may provide an allele-specific count of the number of STR repeats at a particular locus in the genome of the individual.

In some embodiments, the sequencing step (e) is paired-end sequencing, meaning that both ends of a strand are sequenced. In these embodiments, the method comprises, prior to the counting step (f), eliminating sequence reads that do not contain the sequence of a primer used in step (d). In some embodiments, the number of STR repeats counted is validated as being accurate using a sequence read obtained from the other strand, which can be identified because it contains the sequence of the primer used in step (d).

Kits for performing the method are also provided.

BRIEF DESCRIPTION OF THE DRAWINGS

Certain aspects of the following detailed description are best understood when read in conjunction with the accompanying drawings. It is emphasized that, according to common practice, the various features of the drawings are not to scale. On the contrary, the dimensions of the various features are arbitrarily expanded or reduced for clarity. Included in the drawings are the following figures:

FIG. 6A: A pool of oligonucleotides used as templates for gRNA preparation were synthesized using microarray synthesis. The template has four parts which are adapter, T7 promotor, target, and trans-activating CRISPR RNA (tracrRNA) sequences. Two adapter sequences are used to separately prepare gRNAs targeting upstream or downstream of STR targets. Using primers targeting the adapters and tracrRNA sequences, double strand DNA (dsDNA) templates were amplified. Finally, in vitro transcription generated the single strand RNA (ssRNA) products that could be used for the targeted fragmentation after a purification step. The products of PCR amplification (6B) and in vitro transcription (6C) are shown. The templates of downstream-targeting gRNA is longer than that of upstream-targeting gRNA by 4 bases, which is consistent with the gel image of PCR amplicons.

DEFINITIONS

Figure 1:
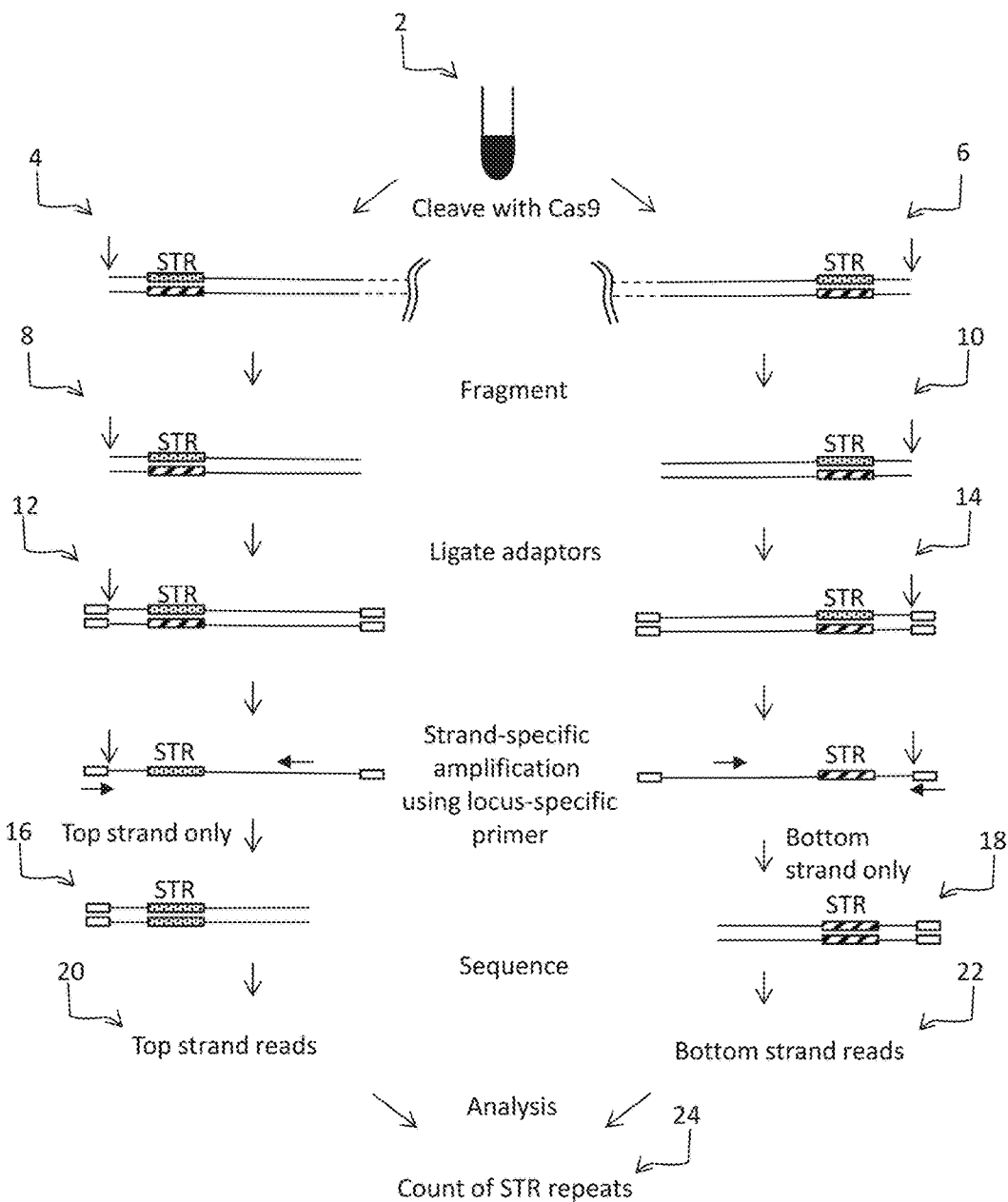
FIG. 1 shows some of the principles of some embodiments of the present method.

Before describing exemplary embodiments in greater detail, the following definitions are set forth to illustrate and define the meaning and scope of the terms used in the description.

Numeric ranges are inclusive of the numbers defining the range. Unless otherwise indicated, nucleic acids are written left to right in 5' to 3' orientation; amino acid sequences are written left to right in amino to carboxy orientation, respectively.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

It must be noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

The term "sample" as used herein relates to a material or mixture of materials, typically, although not necessarily, in liquid form, containing one or more analytes of interest. The nucleic acid samples used herein may be complex in that they contain multiple different molecules that contain sequences. Genomic DNA and cDNA made from mRNA from a mammal (e.g., mouse or human) are types of complex samples. Complex samples may have more then $10^4$, $10^5$, $10^6$ or $10^7$ different nucleic acid molecules. A DNA target may originate from any source such as genomic DNA, cDNA (from RNA) or artificial DNA constructs. Any sample containing nucleic acid, e.g., genomic DNA made from tissue culture cells, a sample of tissue, or an FFPE sample, may be employed herein.

The term "nucleic acid sample," as used herein denotes a sample containing nucleic acids. A nucleic acid sample used herein may be complex in that they contain multiple different molecules that contain sequences. Genomic DNA, RNA (and cDNA made from the same) from a mammal (e.g., mouse or human) are types of complex samples. Complex samples may have more then $10^4$, $10^5$, $10^6$ or $10^7$ different nucleic acid molecules. A target molecule may originate from any source such as genomic DNA, or an artificial DNA construct. Any sample containing nucleic acid, e.g., genomic DNA made from tissue culture cells or a sample of tissue, may be employed herein.

The term "mixture", as used herein, refers to a combination of elements, that are interspersed and not in any particular order. A mixture is heterogeneous and not spatially separable into its different constituents. Examples of mixtures of elements include a number of different elements that are dissolved in the same aqueous solution and a number of different elements attached to a solid support at random positions (i.e., in no particular order). A mixture is not addressable. To illustrate by example, an array of spatially separated surface-bound polynucleotides, as is commonly known in the art, is not a mixture of surface-bound polynucleotides because the species of surface-bound polynucleotides are spatially distinct and the array is addressable.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, or the likes.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., peptide nucleic acid or PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine, thymine, uracil (G, C, A, T and U respectively). DNA and RNA have a deoxyribose and ribose sugar backbone, respectively, whereas PNA's backbone is composed of repeating N-(2-aminoethyl)-glycine units linked by peptide bonds. In PNA various purine and pyrimidine bases are linked to the backbone by methylenecarbonyl bonds. A locked nucleic acid (LNA), often referred to as inaccessible RNA, is a modified RNA nucleotide. The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired. The term "unstructured nucleic acid", or "UNA", is a nucleic acid containing non-natural nucleotides that bind to each other with reduced stability. For example, an unstructured nucleic acid may contain a G' residue and a C' residue, where these residues correspond to non-naturally occurring forms, i.e., analogs, of G and C that base pair with each other with reduced stability, but retain an ability to base pair with naturally occurring C and G residues, respectively. Unstructured nucleic acid is described in US20050233340, which is incorporated by reference herein for disclosure of UNA.

The term "oligonucleotide" as used herein denotes a single-stranded multimer of nucleotides of from about 2 to 200 nucleotides, or up to 500 nucleotides in length. Oligonucleotides may be synthetic or may be made enzymatically, and, in some embodiments, are 30 to 150 nucleotides in length. Oligonucleotides may contain ribonucleotide monomers (i.e., may be oligoribonucleotides) or deoxyribonucleotide monomers, or both ribonucleotide monomers and deoxyribonucleotide monomers. An oligonucleotide may be 10 to 20, 11 to 30, 31 to 40, 41 to 50, 51 to 60, 61 to 70, 71 to 80, 80 to 100, 100 to 150 or 150 to 200 nucleotides in length, for example.

"Primer" means an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Usually primers are extended by a DNA polymerase. Primers are generally of a length compatible with their use in synthesis of primer extension products, and are usually in the range of between 8 to 100 nucleotides in length, such as 10 to 75, 15 to 60, 15 to 40, 18 to 30, 20 to 40, 21 to 50, 22 to 45, 25 to 40, and so on, more typically in the range of between 18 to 40, 20 to 35, 21 to 30 nucleotides long, and any length between the stated ranges. Typical primers can be in the range of between 10 to 50 nucleotides long, such as 15 to 45, 18 to 40, 20 to 30, 21 to 25 and so on, and any length between the stated ranges. In some embodiments, the primers are usually not more than about 10, 12, 15, 20, 21, 22, 23, 24, 25, 26, 27, 28, 29, 30, 35, 40, 45, 50, 55, 60, 65, or 70 nucleotides in length. Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

The term "hybridization" or "hybridizes" refers to a process in which a nucleic acid strand anneals to and forms a stable duplex, either a homoduplex or a heteroduplex, under normal hybridization conditions with a second complementary nucleic acid strand, and does not form a stable duplex with unrelated nucleic acid molecules under the same normal hybridization conditions. The formation of a duplex is accomplished by annealing two complementary nucleic acid strands in a hybridization reaction. The hybridization reaction can be made to be highly specific by adjustment of the hybridization conditions (often referred to as hybridization stringency) under which the hybridization reaction takes place, such that hybridization between two nucleic acid strands will not form a stable duplex, e.g., a duplex that retains a region of double-strandedness under normal stringency conditions, unless the two nucleic acid strands contain a certain number of nucleotides in specific sequences which are substantially or completely complementary. "Normal hybridization or normal stringency conditions" are readily determined for any given hybridization reaction. See, for example, Ausubel et al., Current Protocols in Molecular Biology, John Wiley & Sons, Inc., New York, or Sambrook et al., Molecular Cloning: A Laboratory Manual, Cold Spring Harbor Laboratory Press. As used herein, the term "hybridizing" or "hybridization" refers to any process by which a strand of nucleic acid binds with a complementary strand through base pairing.

A nucleic acid is considered to be "selectively hybridizable" to a reference nucleic acid sequence if the two sequences specifically hybridize to one another under moderate to high stringency hybridization and wash conditions. Moderate and high stringency hybridization conditions are known (see, e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.). One example of high stringency conditions include hybridization at about 42° C. in 50% formamide, 5×SSC, 5×Denhardt's solution, 0.5% SDS and 100 ug/ml denatured carrier DNA followed by washing two times in 2×SSC and 0.5% SDS at room temperature and two additional times in 0.1×SSC and 0.5% SDS at 42° C.

The term "duplex," or "duplexed," as used herein, describes two complementary polynucleotides that are base-paired, i.e., hybridized together.

The term "amplifying" as used herein refers to the process of synthesizing nucleic acid molecules that are complementary to one or both strands of a template nucleic acid. Amplifying a nucleic acid molecule may include denaturing the template nucleic acid, annealing primers to the template nucleic acid at a temperature that is below the melting temperatures of the primers, and enzymatically elongating from the primers to generate an amplification product. The denaturing, annealing and elongating steps each can be performed one or more times. In certain cases, the denaturing, annealing and elongating steps are performed multiple times such that the amount of amplification product is increasing, often times exponentially, although exponential amplification is not required by the present methods. Amplification typically requires the presence of deoxyribonucleoside triphosphates, a DNA polymerase enzyme and an appropriate buffer and/or co-factors for optimal activity of the polymerase enzyme. The term "amplification product" refers to the nucleic acid sequences, which are produced from the amplifying process as defined herein.

The terms "determining", "measuring", "evaluating", "assessing," "assaying," and "analyzing" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

The term "using" has its conventional meaning, and, as such, means employing, e.g., putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

The term "genomic region", as used herein, refers to a region of a genome, e.g., an animal or plant genome such as the genome of a human, monkey, rat, fish or insect or plant.

The term "terminal nucleotide", as used herein, refers to the nucleotide at either the 5' or the 3' end of a nucleic acid strand. The nucleic acid strand may be in double-stranded (i.e., duplexed) or in single-stranded form.

The term "ligating", as used herein, refers to the enzymatically catalyzed joining of the terminal nucleotide at the 5' end of a first DNA molecule to the terminal nucleotide at the 3' end of a second DNA molecule.

A "plurality" contains at least 2 members. In certain cases, a plurality may have at least 2, at least 5, at least 10, at least 100, at least 100, at least 10,000, at least 100,000, at least $10^6$, at least $10^7$, at least $10^8$ or at least $10^9$ or more members.

If two nucleic acids are "complementary", they hybridize with one another under high stringency conditions. The term "perfectly complementary" is used to describe a duplex in which each base of one of the nucleic acids base pairs with a complementary nucleotide in the other nucleic acid. In many cases, two sequences that are complementary have at least 10, e.g., at least 12 or 15 nucleotides of complementarity.

The term "strand" as used herein refers to a nucleic acid made up of nucleotides covalently linked together by covalent bonds, e.g., phosphodiester bonds. In a cell, DNA usually exists in a double-stranded form, and as such, has two complementary strands of nucleic acid referred to herein as the "top" and "bottom" strands. In certain cases, complementary strands of a chromosomal region may be referred to as "plus" and "minus" strands, the "first" and "second" strands, the "coding" and "noncoding" strands, the "Watson" and "Crick" strands or the "sense" and "antisense" strands. The assignment of a strand as being a top or bottom strand is arbitrary and does not imply any particular orientation, function or structure. The nucleotide sequences of the first strand of several exemplary mammalian chromosomal regions (e.g., BACs, assemblies, chromosomes, etc.) is known, and may be found in NCBI's Genbank database, for example.

The term "top strand," as used herein, refers to either strand of a nucleic acid but not both strands of a nucleic acid. When an oligonucleotide or a primer binds or anneals "only to a top strand," it binds to only one strand but not the other. The term "bottom strand," as used herein, refers to the strand that at least partly complementary to the "top strand." When an oligonucleotide binds or anneals "only to one strand," it binds to only one strand, e.g., the first or second strand, but not the other strand. In certain cases and as will be described in greater detail below, two strands may be annealed to one another in a duplex but there may be part of the duplex that is not annealed (e.g., because the sequences are not complementary). In these cases, the strands that are not annealed may still be referred to as being "top" and "bottom" strands because they are covalently linked to strands that are annealed to one another.

The term "strand-specific sequencing", as used herein, refers to sequencing the top and bottom strands of an initial fragment of double stranded DNA in spatially distinct sequencing reactions, where the top and bottom sequence reads can be paired with each other and compared during data analysis. Paired-end sequencing, on the other hand, is not bidirectional sequencing because, in paired end sequencing, both ends of the sequenced amplicon are derived from only one strand of an initial fragment.

The term "covalently linking" refers to the production of a covalent linkage between two separate molecules, e.g., the top and bottom strands of a double stranded nucleic acid. Ligating is a type of covalent linking.

The term "denaturing," as used herein, refers to the separation of at least a portion of the base pairs of a nucleic acid duplex by placing the duplex in suitable denaturing conditions. Denaturing conditions are well known in the art. In one embodiment, in order to denature a nucleic acid duplex, the duplex may be exposed to a temperature that is above the Tm of the duplex, thereby releasing one strand of the duplex from the other. In certain embodiments, a nucleic acid may be denatured by exposing it to a temperature of at least 90° C. for a suitable amount of time (e.g., at least 30 seconds, up to 30 mins). In certain embodiments, fully denaturing conditions may be used to completely separate the base pairs of the duplex. In other embodiments, partially denaturing conditions (e.g., with a lower temperature than fully denaturing conditions) may be used to separate the base pairs of certain parts of the duplex (e.g., regions enriched for A-T base pairs may separate while regions enriched for G-C base pairs may remain paired.) Nucleic acid may also be denatured chemically (e.g., using urea or NaOH).

The term "sequencing", as used herein, refers to a method by which the identity of at least 10 consecutive nucleotides (e.g., the identity of at least 20, at least 50, at least 100 or at least 200 or more consecutive nucleotides) of a polynucleotide are obtained.

The term "next-generation sequencing" refers to the so-called parallelized sequencing-by-synthesis or sequencing-by-ligation platforms currently employed by Illumina, Life Technologies, and Roche etc. Next-generation sequencing methods may also include nanopore sequencing methods or electronic-detection based methods such as Ion Torrent technology commercialized by Life Technologies.

The term "extending", as used herein, refers to the extension of a primer by the addition of nucleotides using a polymerase. If a primer that is annealed to a nucleic acid is extended, the nucleic acid acts as a template for extension reaction.

The term "barcode sequence" or "molecular barcode", as used herein, refers to a unique sequence of nucleotides used to (a) identify and/or track the source of a polynucleotide in a reaction and/or (b) count how many times an initial molecule is sequenced (e.g., in cases where substantially every molecule in a sample is tagged with a different sequence, and then the sample is amplified). A barcode sequence may be at the 5'-end, the 3'-end or in the middle of an oligonucleotide, or both the 5' end and the 3' end. Barcode sequences may vary widely in size and composition; the following references provide guidance for selecting sets of barcode sequences appropriate for particular embodiments: Brenner, U.S. Pat. No. 5,635,400; Brenner et al, Proc. Natl. Acad. Sci., 97: 1665-1670 (2000); Shoemaker et al, Nature Genetics, 14: 450-456 (1996); Morris et al, European patent publication 0799897A1; Wallace, U.S. Pat. No. 5,981,179; and the like. In particular embodiments, a barcode sequence may have a length in range of from 4 to 36 nucleotides, or from 6 to 30 nucleotides, or from 8 to 20 nucleotides.

As used herein, the term "PCR reagents" refers to all reagents that are required for performing a polymerase chain reaction (PCR) on a template. As is known in the art, PCR reagents essentially include a first primer, a second primer, a thermostable polymerase, and nucleotides. Depending on the polymerase used, ions (e.g., $Mg^{2+}$) may also be present. PCR reagents may optionally contain a template from which a target sequence can be amplified.

The term "adjacent to" refers to a distance of less than the longest dimension of a nucleotide. The term "ligatably adjacent to" means that two nucleotides are immediately adjacent to one another on a strand with no intervening nucleotides.

The term "tailed", in the context of a tailed primer or a primer that has a 5' tail, refers to a primer that has a region (e.g., a region of at least 12-50 nucleotides) at its 5' end that does not hybridize to the same target as the 3' end of the primer.

The term "distinguishable sequences" refers to sequences that are different to one another.

The term "target nucleic acid" as use herein, refers to a polynucleotide of interest under study.

The term "target nucleic acid molecule" refers to a single molecule that may or may not be present in a composition with other target nucleic acid molecules. An isolated target nucleic acid molecule refers to a single molecule that is present in a composition that does not contain other target nucleic acid molecules.

The term "variable", in the context of two or more nucleic acid sequences that are variable, refers to two or more nucleic acids that have different sequences of nucleotides relative to one another. In other words, if the polynucleotides of a population have a variable sequence, then the nucleotide sequence of the polynucleotide molecules of the population varies from molecule to molecule. The term "variable" is not to be read to require that every molecule in a population has a different sequence to the other molecules in a population.

The term "adaptor" refers to a nucleic acid that can be joined, either using a ligase or a transposase-mediated reaction, to at least one strand of a double-stranded DNA molecule. In one embodiment, an adaptor may be a Y-adaptor. As would be apparent, one end of an adaptor may contain a transposon end sequence, or may be designed to be compatible with overhangs made by cleavage by a restriction enzyme, or it may have blunt ends or a 5' T overhang. The term "adaptor" refers to molecules that are at least partially double-stranded. An adaptor may be 40 to 150 bases in length, e.g., 50 to 120 bases, although adaptors outside of this range are envisioned.

The term "adaptor-tagged," as used herein, refers to a nucleic acid that has been tagged by an adaptor. The adaptor can be joined to a 5' end and/or a 3' end of a nucleic acid molecule.

The term "tagged DNA" as used herein refers to DNA molecules that have an added adaptor sequence, i.e., a "tag" of synthetic origin. An adaptor sequence can be added (i.e., "appended") by ligation, by a transposase, or by primer extension.

The term "Y-adaptor" refers to an adaptor that contains: a double-stranded region and a single-stranded region in which the opposing sequences are not complementary. The end of the double-stranded region can be joined to target molecules such as double-stranded fragments of genomic DNA, e.g., by ligation or a transposase-catalyzed reaction. Each strand of an adaptor-tagged double-stranded DNA that has been ligated to a Y adaptor is asymmetrically tagged in that it has the sequence of one strand of the Y-adaptor at one end and the other strand of the Y-adaptor at the other end. Amplification of nucleic acid molecules that have been joined to Y-adaptors at both ends results in an asymmetrically tagged nucleic acid, i.e., a nucleic acid that has a 5' end containing one tag sequence and a 3' end that has another tag sequence.

As used herein, the term "short tandem repeat' refers to a microsatellite repeat, composed of a unit of two to thirteen nucleotides repeated up to hundreds of times (usually 5-50 times) in a row in genomic DNA. The number of tandem repeats at any STR locus may vary from individual to individual. STR analysis measures the exact number of repeating units in a locus. See, e.g., Richard et al. (Micr. Mol. Bio. Rev 2008 72: 686-727).

As used herein, the term "separately digesting" refers to two or more different cleavage reactions.

As used herein, the term "RNA-guided nuclease" refers to a Type II CRISPR/Cas-based system that is composed of two components: a nuclease (e.g., a Cas9 endonuclease or variant thereof) that cleaves the target DNA and a guide RNA (gRNA) that targets the nuclease to a specific site in the target DNA. See, e.g., Hsu et al (Nature Biotechnology 2013 31: 827-832).

As used herein, the term "portion" refers to a part (e.g., an aliquot) of a sample.

As used herein, the term, "defined site" refers to a selected sequence.

As used herein, the term, "selectively amplifying" refers to an amplification reaction (e.g., a PCR reaction) in which only chosen sequences are amplified.

DETAILED DESCRIPTION

FIG. 1 illustrates some of the principles of some embodiments of the method. In these embodiments, the method may comprise (a) separately digesting: (i) a first portion of a genomic sample 2 from an individual, at a defined site that is upstream (e.g., 10-400 bases, or 20-100 bases upstream) of an STR using an RNA-guided nuclease; and (ii) a second portion of sample 2, at a defined site that is downstream (e.g., 10-400 bases, or 20-100 bases upstream) of the STR using an RNA-guided nuclease, to produce first digestion products 4 and second digestion products 6. This step may be done in two separate reactions and the digestion products may be combined for the remainder of the steps. In other words, the method may comprise pooling the products of step (a), (b), (c) or (d) (described below). FIG. 1 schematically illustrates the molecules as separate entities although they can be combined in the same reaction. After the digestion products are optionally combined, the next step may comprise: (b) fragmenting the first and second digestion products to produce first fragmentation products 8 and second fragmentation products 10, which (c) products are ligated to an adaptor (e.g., a Y-adaptor) to produce first ligation products 12 and second ligation products 14;

In some embodiments, the fragmenting may be done mechanically (e.g., by sonication, nebulization, or shearing) or using a double stranded DNA "dsDNA" fragmentase enzyme (New England Biolabs, Ipswich Mass.). In some embodiments, after the DNA is fragmented, the ends are polished and A-tailed prior to ligation to the adaptor. Alternatively, the ends may be polished and ligated to adaptors in a blunt-end ligation reaction. In these embodiments, these steps may be mediated by a transposase (see, e.g., Caruccio, Methods Mol. Biol. 2011; 733:241-55), in which case the steps may be done simultaneously, i.e., in the same reaction using a process that is often referred to as "tagmentation". The fragments in the initial sample may have a median size that is below 1 kb (e.g., in the range of 50 bp to 500 bp, or 80 bp to 400 bp), although fragments having a median size outside of this range may be used.

Figure 3:
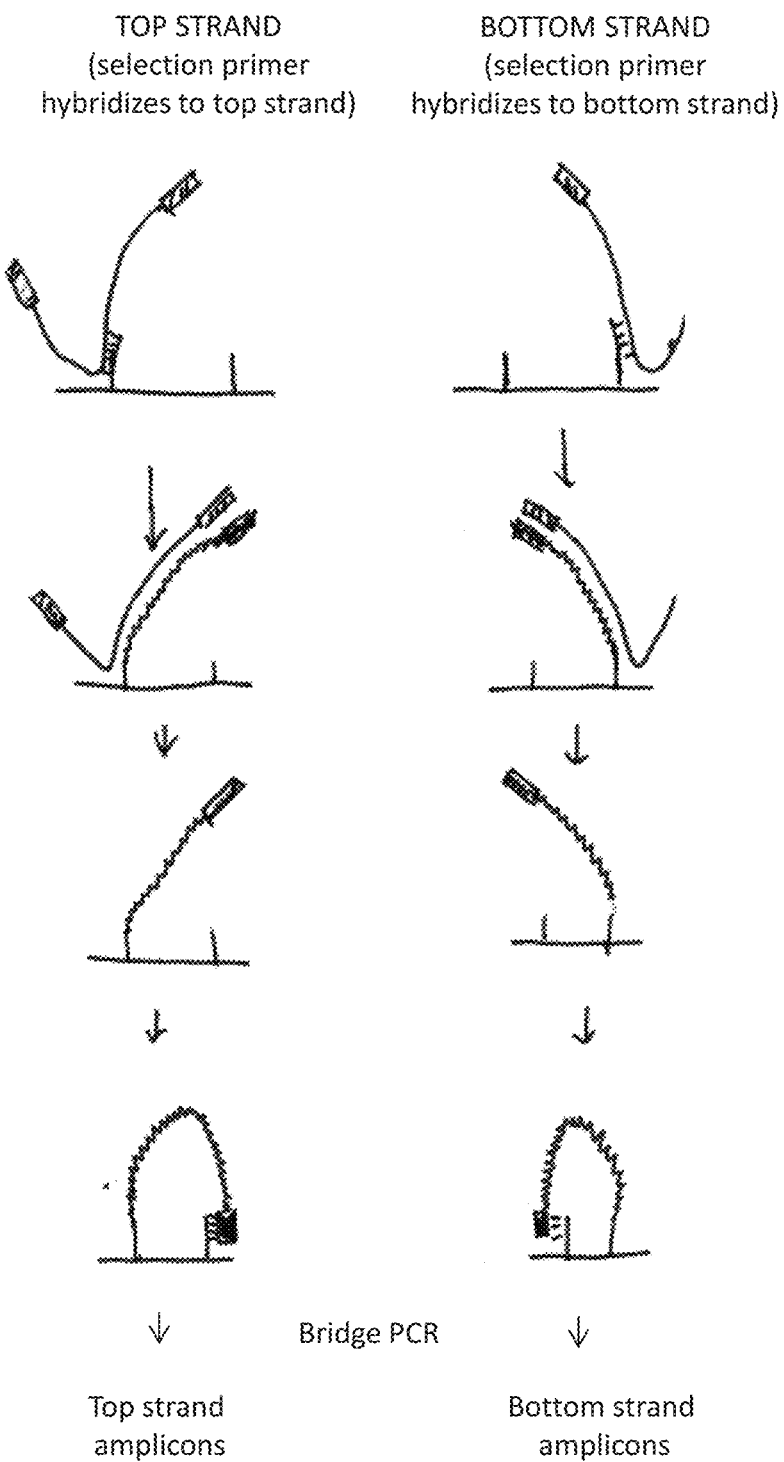
FIG. 3 shows how strand-specific PCR can be done on a solid support.
Figure 4:
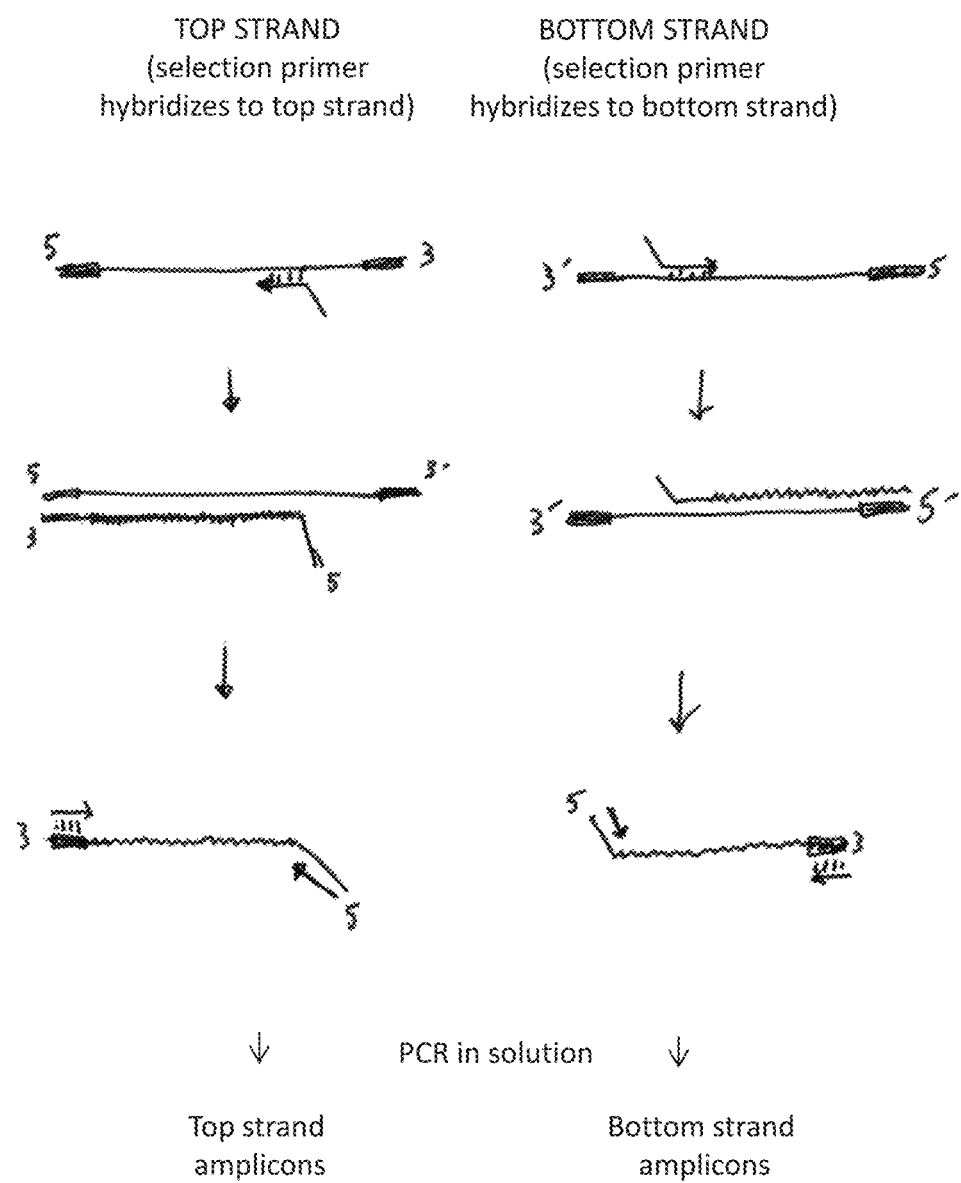
FIG. 4 shows how strand-specific PCR can be done in solution.

Next, the method may comprise (d) selectively amplifying, using strand-specific primers (one for each strand) and a primer that hybridizes to the adaptor: (i) part of the top strand but not the bottom strand of the first ligation products to produce top strand products 16; and (ii) part of the bottom strand but not the top strand of the second ligation products to produce bottom strand products 18. As shown in FIG. 1, the strand-specific primers are designed to hybridize to sites on the other side of the STR relative to the nuclease cleavage site. This step may done by hybridizing the top and bottom strands to strand-specific primers that are tethered to a solid support (as shown in FIG. 3) or in solution (as shown in FIG. 4), and then amplifying the captured material using a second primer that hybridizes to the adaptor (which may be tethered to a support or in solution, as desired). The solid support based method (as shown in FIG. 3) is described in more detail in, e.g., Hopmans (Nucleic Acids Res. 2014 42: e88), Myllykangas et al (Nat. Biotechnol. 2011 29:1024-7) and US20120157322, which are incorporated by reference for disclosure of that method. Likewise, some of the principles of the in-solution based method (as shown in FIG. 4) are described in US20130231253 which is incorporated by reference for disclosure of that method.

As would be apparent, the primers used for amplification may be compatible with use in any next generation sequencing platform in which primer extension is used, e.g., Illumina's reversible terminator method, Roche's pyrosequencing method (454), Life Technologies' sequencing by ligation (the SOLiD platform), Life Technologies' Ion Torrent platform or Pacific Biosciences' fluorescent base-cleavage method. Examples of such methods are described in the following references: Margulies et al (Nature 2005 437: 376-80); Ronaghi et al (Analytical Biochemistry 1996 242: 84-9); Shendure (Science 2005 309: 1728); Imelfort et al (Brief Bioinform. 2009 10:609-18); Fox et al (Methods Mol Biol. 2009; 553:79-108); Appleby et al (Methods Mol Biol. 2009; 513:19-39) English (PLoS One. 2012 7: e47768) and Morozova (Genomics. 2008 92:255-64), which are incorporated by reference for the general descriptions of the methods and the particular steps of the methods, including all starting products, reagents, and final products for each of the steps. Indeed, if the products are amplified on a solid support (e.g., using an Illumina flow cell), then the amplicons may be sequenced in place on the substrate, as described in Hopmans and Myllikangas above, which avoids many of the effects of stutter and recombination that occur during in-solution PCR.

Next, the method may comprise (e) sequencing at least some of the amplification products of step (d) to produce a plurality of top strand reads 20 and a plurality of bottom strand reads 22. The sequencing step may be done using any convenient next generation sequencing method and may result in at least 10,000, at least 50,000, at least 100,000, at least 500,000, at least 1M at least 10M at least 100M or at least 1B sequence reads. In many cases, the reads are paired-end reads.

Next, the sequence reads are analyzed to (f) provide a count of the number of STR repeats in a sequence read (or group of the same) of step (e), thereby providing an allele-specific count 24 of the number of STR repeats at a particular locus in the genome of the individual.

Figure 2:
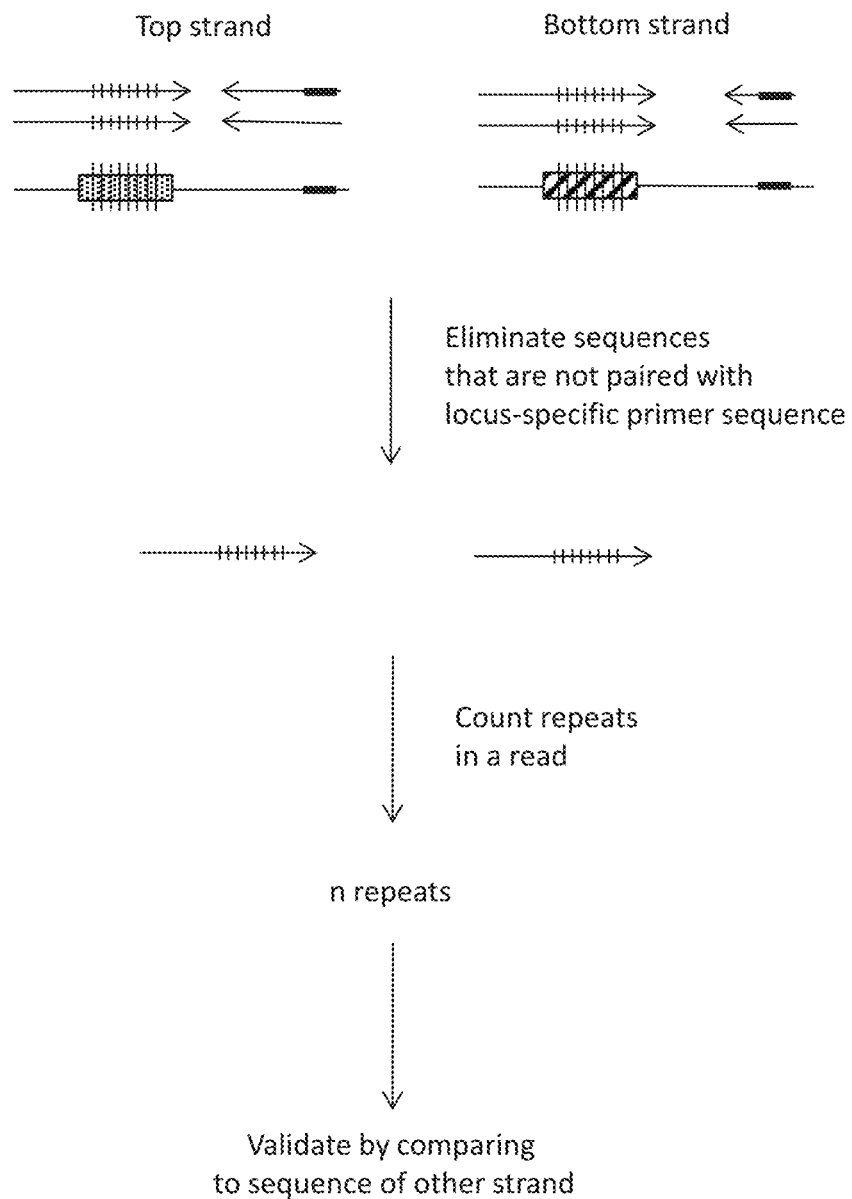
FIG. 2 shows one implementation of a bioinformatics analysis workflow.

The sequence reads may be processed in any convenient way. In some embodiments the initial processing of the sequence reads may include identification of molecular barcodes (including sample indexing sequences) and/or trimming reads to remove low quality or adaptor sequences. The sequence reads may be analyzed by a computer and, as such, instructions for performing the steps set forth below may be set forth as programming that may be recorded in a suitable physical computer readable storage medium. The general principles of some of the analysis steps are illustrated in FIG. 2 and shown below.

In some embodiments, the sequencing step (e) is paired-end sequencing (meaning that each amplicon is amplified from both ends, to provide sequences that may or may not be overlapping), and, in these embodiments, the method may comprise, prior to the counting step (f), eliminating sequence reads that do not contain the sequence of a primer used in step (d). In other words, if the read 1 of the paired end sequence starts from the cleavage site for the nuclease, then the other end serves as the capture sequence for strand-specific amplification and, as such, all on-target sequence reads should contain the capture sequence. As such, on-target sequence reads can be selected because they contain a capture sequence. In some cases, the number of repeats in a selected sequence read can be counted, and validated. In some cases, the number of repeats in a sequence read can be validated by comparing it to other sequence reads that have the same capture sequence and, in some cases, the number of repeats in a sequence read can be validated as being accurate only if the number of repeats matches the number of repeats counted from a read from the other strand. In other words, for any one STR locus, the capture sequence for the top strand is known and the capture sequence for the bottom strand is known, and therefore sequences derived from the top strand and the bottom strand of a particular STR can be linked to one another computationally by identifying a matching pair of capture sequences. In other words, the capture sequences not only allow off-target sequences to be eliminated, but they also serve to pair the top and bottom strand sequence reads to one another. As would be apparent, the method may further comprise analyzing the numbers of STR repeats in further sequence reads, and validating those numbers as being accurate only if the further sequence reads match sequence reads from the other strand. This analysis allows one to determine whether the individual is homozygous for a particular allele of the STR, or heterozygous for different alleles of the STR.

In some embodiments, the locus-specific primer used in step (d) may bind to a site, that is on the other side but proximal to, of potential sequence variation (e.g., a single nucleotide polymorphism or indel) and, as such, the allele of a sequence variation linked to the STR can be determined be examining the paired-end sequence (read 2, if the STR is sequenced using read 1 or vice versa). In these embodiments, the sequencing step (e) is paired-end sequencing, and the method may comprise analyzing the paired end read to determine the allele of a sequence variation that is linked to the STR.

In some embodiments, the method may comprise analyzing a plurality of STRs (at least 10, at least 50, at least 100, at least 200, at least 500, at least 1,000, at least 5000 or at least 10,000 STRs) in parallel using the above-described method, thereby producing an STR fingerprint (a list of the number of repeats present at each STR locus analyzed and whether the STR alleles detected are homozygous or heterozygous) for an individual.

After an STR fingerprint for an individual has been obtained, it can be compared to the STR fingerprint from a second individual, e.g., to determine if the individuals are related. In certain cases, the STR fingerprint is an STR fingerprint obtained from a sample (e.g., a sample of blood or semen) obtained from a potential crime scene, thereby allowing one to determine if the individual was at the crime scene.

In other embodiments, the sample may be from a cancer biopsy and, in some cases, the method may be used to analyze cancer biopsies obtained from different locations in the same individual, different locations in a single tumor, or different times during progression of a tumor. STRs are highly unstable in cancerous cells (i.e., the number of repeats in many STRs changes rapidly during cancer progression, unlike normal cells). In these embodiments, the method may be used to perform a clonal analysis of cancer progression. In these embodiments, the method may further comprise comparing the STR fingerprint for the cancer biopsy to a STR fingerprint for a second cancer biopsy, to provide a clonal analysis of cancer progression.

In certain embodiments, the adaptor added to the sample may have a sample identifier sequence (an indexer), thereby allowing that sample to be combined with indexed samples from other individuals (e.g., up to 10, 50, 100, 200 or 1,000 or more individuals) prior to sequencing, thereby allowing one to obtain a STR fingerprint for those individuals in a single sequencing run.

The following patent applications are incorporated by reference for all purposes, including a description of OS- SEQ, for definitions and for general description of some of the steps and reagents used in the method: US20120157322, US20140163900 and US20150037791.

Kits

Also provided by the present disclosure are kits for practicing the subject method as described above. In certain embodiments, a subject kit may contain: a) an RNA-directed nuclease (e.g., cas9 protein); b) guide RNAs that target the nuclease to sites upstream from a plurality of STRs; c) guide RNAs that target the nuclease sites downstream from a plurality of STRs; d) adaptors for ligating onto the fragments (which may be Y adaptors although this is not required), e) strand-specific primers that hybridize to the top strand of fragments that contain the STRs, f) strand-specific primers that hybridize to the bottom strand of fragments that contain the STRs; and g) a primer that hybridizes to the adaptor, where the strand-specific primers (or the reverse complement of the same) and the primer that hybridizes to the adaptor can amplify the STR-containing fragments in a strand-specific manner, as described above. Further details of the components of this kit are described above. The kit may also contain other reagents described above and below that may be employed in the method, e.g., a ligase, polymerase, etc., depending on how the method is going to be implemented.

In addition to above-mentioned components, the subject kit further includes instructions for using the components of the kit to practice the subject method. The instructions for practicing the subject method are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

In order to further illustrate the present invention, the following specific examples are given with the understanding that they are being offered to illustrate the present invention and should not be construed in any way as limiting its scope.

EXAMPLES

The following examples are given for the purpose of illustrating various embodiments of the invention and are not meant to limit the invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

A method referred to as "STR-Seq", a massively parallel sequencing approach that generates microsatellite-spanning sequence reads with high coverage and accurate genotypes, was developed. As part of the library preparation process a targeted DNA fragmentation process with CRISPR/Cas9 developed, thus increasing the number of DNA molecules that have an intact microsatellite sequence. An amplification-free method was applied for targeted STR sequencing that results in each sequence read corresponding to a single DNA molecule without the use of molecular barcodes. Correspondingly, amplification artifacts are reduced. Further, a novel bioinformatics pipeline was developed for quantifying STR motifs and associated SNPs in phase with the STR, thus generating haplotypes. It is demonstrated that STR-Seq is highly accurate using a ground truth set of previously genotyped samples, has higher throughput than other methods, provides phased STR/SNP haplotypes and can resolve individual-specific haplotypes at minor allelic fractions of 0.1% in genetic mixtures.

Materials and Methods

Genomic DNA Samples:

Genomic DNA extractions from HapMap (NA12878, NA12891, and NA12892) and Human Genome Diversity Project (HGDP00457, HGDP00474, HGDP00924, HGDP00925, HGDP00926, HGDP00927, HGDP00928, HGDP00929, HGDP00932, HGDP01028, HGDP01030, HGDP01032, HGDP01034, HGDP01035, HGDP01414, and HGDP01417) individuals were obtained from the Coriell Institute for Medical Research (Camden, N.J.) and the Foundation Jean Dausset—Centre d'Etude du Polymorphisme Humain (Paris, France), respectively. Genomic DNA was quantitated using the Qubit dsDNA BR assay kit (Thermo Fisher Scientific, Waltham, Mass.). DNA sample size distribution was assessed with the LabChip GX (Perkin-Elmer, Waltham, Mass.) following the manufacturer's protocol.

Primer Probe Design for STRs:

The locations of 962,714 tandem repeats were obtained from a file called "simpleRepeat.txt.gz" at UCSC Genome Browser ("http:" followed by "//hgdownload.soe.ucsc." followed by "edu/goldenPath/hg19/database"). As an additional quality control, 950,265 repeats located on canonical chromosomes were selected. Candidate STR loci were limited to short repeats (<=100 bp), to enable a single Illumina sequencing read to cover the entire STR. Based on this size criteria, 743,796 STRs were identified from the human genome reference (hg19).

Additional design criteria were used to increase the probability of an informative SNP being located in close proximity to the STR locus. For this purpose, NCBI dbSNP Build 138 was used, which was downloaded from UCSC Genome Browser ("http:" followed by "//hgdownload.soe.ucsc." followed by "edu/goldenPath/hg19/database"). This data set was comprised of a total of 14,017,609 SNPs that were validated by one of the groups: 1,000 Genomes Project, the Hapmap Project or the submitter. Among these validated SNPs, 13,737,549 SNPs were located on canonical chromosomes.

Of the identified short repeats which totaled 743,796, 512,612 were identified that had at least one validated SNP within 100 bp. Probes were designed for a total of 10,090 of these STRs. To determine the STRs with the highest probability of having an informative SNP allele, SNPs that had high population allele frequencies across different populations were selected—if the additive genotype frequency was greater than 1.0, this SNP was included. This ethnic specific genotype population was ascertained from dbSNP138. Using this approach, 2,191 STRs that were proximal to a reported SNP position were identified.

Among the 2,191 STRs, 964 fulfilled the criteria: repeat unit sizes of 2 to 5 bp, an 80% probability of matching, a 10% probability of an indel, and minimum alignment scores determined for each repeat unit size (2-22, 3-28, 4-28, 5-32, and 6-34). All the information was determined by Tandem Repeat Finder (Benson, Nucleic Acids Research, 27: 573-580, 1999) and downloaded from the UCSC Genome Browser.

Generating Primer Probe Oligonucleotides:

Primer probe pools were prepared either from column- or array-synthesis (Table 1). For Assay 1, primer probes were column-synthesized at the Stanford Genome Technology Center (Palo Alto, Calif.) and combined to generate an equimolar pool where each oligonucleotide was at the same individual concentration. 1,365 primer-probes were designed to analyze 491 STR loci that had been previously genotyped and were pooled with 424 primer-probes targeting other STR loci, as well as 466 primer-probes for exons (Assay 1; Table 1). Primer-probe oligonucleotides targeting exons were included as a subset to provide more sequence diversity and improve the base calling.

TABLE 1

Description of STR-Seq Assays

| Assay version | Assay 1 | Assay 2 |
|---|---|---|
| Total STR targets | 700 | 2,370 |
| gRNA-targeted | 520 | 1,729 |
| CODIS STRs | 19 | 18 |
| CE genotyped STRs | 491 | 19 |
| Markers for microsatellite instability | 182 | 136 |
| STR by Wilems et al. | 505 | 964 |
| STR-SNP | 3 | 918 |
| Homopolymer-SNP | 0 | 181 |
| Candidate STR-SNP | 0 | 1,092 |
| Number of primer probes | 2,255 | 5,152 |
| Oligonucleotide synthesis method | Column-synthesis | Microarray |

Figure 5:
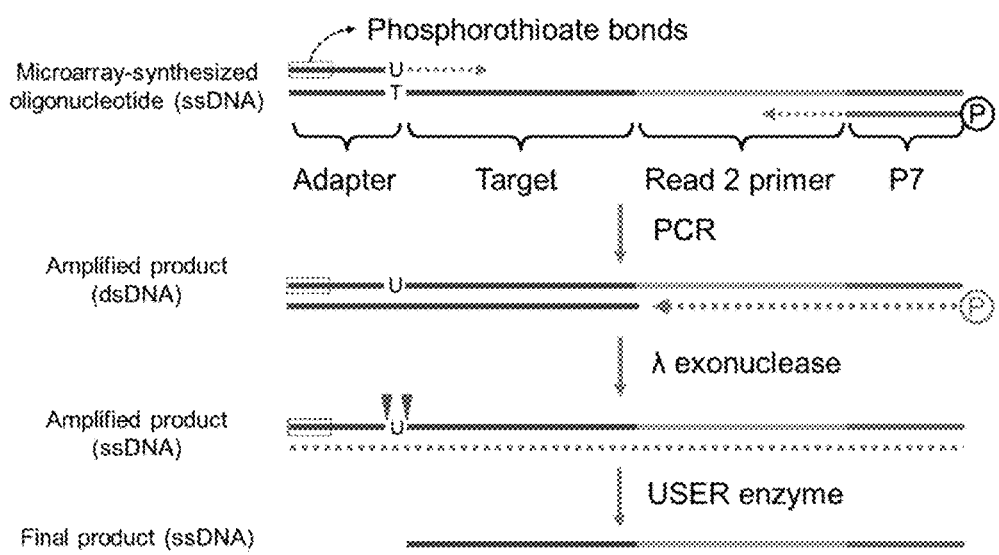
FIG. 5 shows an embodiment of the preparation of primer probe pool from microarray-synthesis. 5A: The STR-Seq primer probes were prepared by three steps which were amplification using modified primers and two enzymatic reactions to get single-stranded final product. First, using modified primers, microarray-synthesized oligonucleotides are amplified. Forward primer has uracil base at the 3' end, by which the adapter sequence becomes detachable after the amplification. In addition, the forward primer has six phosphorothioate bonds at the 5' end which prevent the strands extend from the primer being processed by λ, exonuclease. On the other hand, reverse primer has 5' phosphate, and a strand extend from the reverse primer can easily be eliminated. Second step hydrolyzes the strands extended from reverse primer, and this step kills almost every non-target strand. Finally, the last step detaches the adapter sequence from the target strand, and after overnight incubation with USER enzyme, only small amount of unprocessed DNA are left. 5B: Gel image of denaturing polyacrylamide gel electrophoresis (PAGE) analysis for ssDNA shows the product from each step. Reduced band intensity after λ, exo treatment was noted after the antisense strand digestion (lane 2). A portion of adapter-attached single strand intermediates are still visible when only 1 hr of USER enzyme incubation is used (lane 3). Disappearance of longer fragment after overnight incubation with USER enzyme (lane 4) supports the optimized reaction condition used in this study. Detached adapter fragment was visible for both the products treated with USER enzyme (lanes 3 and 4). Fragment sizes of probe and adapter are 101 nt and 23 nt, respectively.
Figure 5:
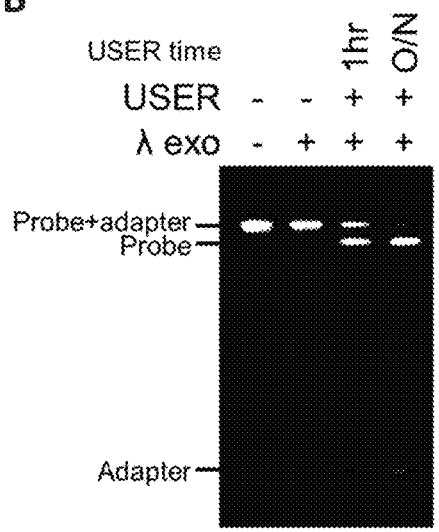

For Assay 2, array-synthesized oligonucleotides (CustomArray, Bothell, Wash.) that were amplified and then processed to generate single stranded DNA for flowcell modification were used. FIG. 5 shows the preparation of primer probe pools from array-synthesized oligonucleotides. Three steps that included amplification using modified primers and two enzymatic reactions were used to get the single-stranded final product (FIG. 5A). The modified primers were synthesized with polyacrylamide gel electrophoresis purification (Integrated DNA Technologies, Corallville, Iowa). The forward primer (5'-A*A*T*G*A*T*ACGGCGACGGATCAAGU-3' (SEQ ID NO:1)) had a uracil base at the 3' end and six phosphorothioate bonds (indicated by *) at the 5' end. The reverse primer (5'-/5Phos/CAAGCAGAAGACGGCATACGAGAT-3' (SEQ ID NO:2)) had a 5' phosphate. Two ng of the original oligonucleotide pool was amplified in a 50-µl reaction mixture including 25 U AmpliTaq Gold DNA polymerase, 1x Buffer I with 1.5 mM MgCl$_2$ (Thermo Fisher Scientific), 1 µM of each primer, 0.2 mM dNTP mixture (New England Biolabs, Ipswich, Mass.). Initially, the reaction was denatured at 95° C. for 10 min, followed by 35 cycles of 15 sec of 95° C., 30 sec of 65° C. and 30 sec of 72° C. The final steps for amplification involved an incubation at 72° C. for 1 min and cooling to 4° C. The amplified product was purified with AMPure XP beads (Beckman Coulter, Brea, Calif.) in a bead solution to sample ratio of 1.8, and then used for next steps. The purified 40-µl dsDNA amplicon was mixed with 10-µl reaction mixture containing 12.5 Uλ exonuclease and 1x reaction buffer (New England Biolabs), and incubated at 37° C. for 2 hours for digestion of strands extended from the reverse primer. The reaction was stopped by heat inactivation at 80° C. for 20 min. 2.7 U of USER enzyme (New England Biolabs) in 1x λ exonuclease reaction buffer was added to the single-stranded product, followed by incubation at 37° C. overnight. The final product was mixed with 3x volume of AMPure XP bead solution and 1x volume of isopropanol. Afterwards, the beads were washed twice by 90% ethanol, and eluted in 20 µl of 10 mM Tris buffer. A Qubit ssDNA assay kit (Thermo Fisher Scientific) was used to quantify the purified product. Denaturing gel electrophoresis was performed using Novex 15% TBE-Urea gel (Thermo Fisher Scientific) to confirm size of final product (FIG. 5B).

Figure 6:
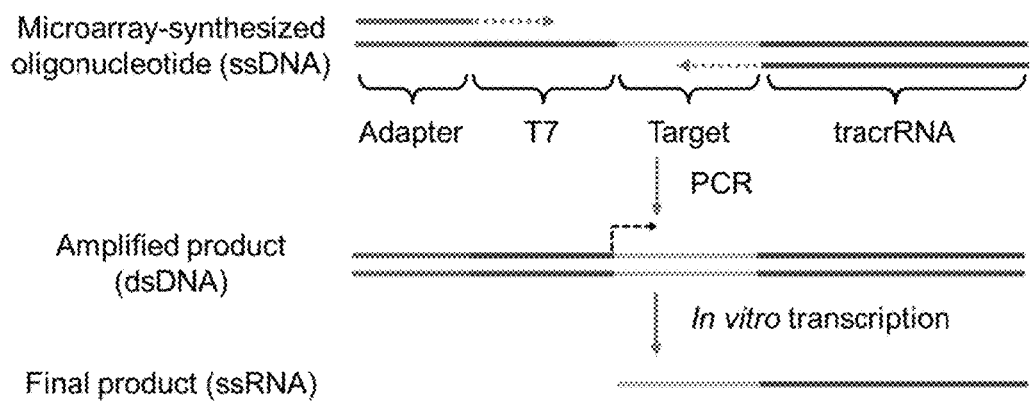
FIG. 6 shows one embodiment of the preparation of gRNA.
Figure 6:
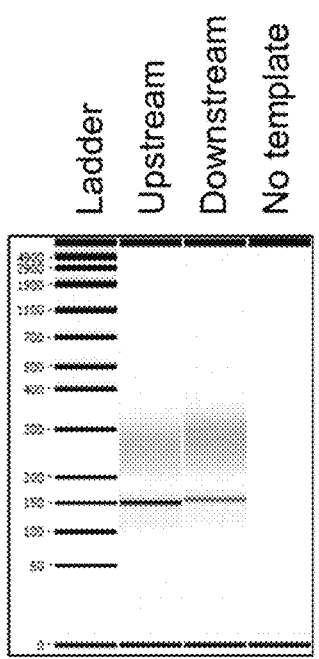
Figure 6:
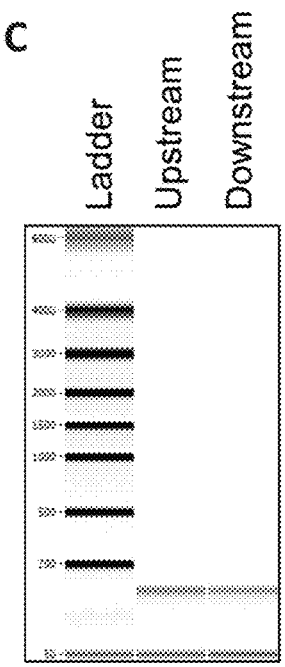

In Vitro Guide RNA Preparation:

A pool of 8,348 guide RNAs targeting 2,098 STRs was prepared from an array-synthesized oligonucleotide pool. The synthesized oligonucleotide consisted of four components: adapter, T7 promoter, target-specific, trans-activating CRISPR RNA (tracrRNA) regions. Because two separate pools targeting upstream or downstream regions of STRs were required, two different adapters were added according to their target orientation. Forward primers (5'-GAGCT-TCGGTTCACGCAATG-3' (SEQ ID NO:3) and 5'-CAAGCAGAAGACGGCATACGAGAT-3' (SEQ ID NO:2)) matching to the adapter sequences and a reverse primer (5'-AAAGCACCGACTCGGTGC-CACTTTTTCAAGTTGATAACGGACTAGCCTTATTT-TAAC TTGCTATTTCTAGCTCTAAAAC-3' (SEQ ID NO:4)) complementary to the tracrRNA sequence were synthesized by Integrated DNA Technologies and used for initial amplification. FIG. 6 summarizes the preparation process for the guide RNA pool from array-synthesized oligonucleotides. Two ng input oligonucleotide pool was amplified in a 25-µl reaction mixture including 1x Kapa HiFi Hot Start Mastermix (KapaBio systems, Woburn, Mass.) and 1 µM of each primer. The reaction was initially denatured at 95° C. for 2 min, followed by 25 cycles of 20 sec of 98° C., 15 sec of 65° C. and 15 sec of 72° C. The final steps for amplification involved an incubation at 72° C. for 1 min and cooling to 4° C. The amplified product was purified with AMPure XP beads in a bead solution to sample ratio of 1.8, and then used for next steps. Two hundred ng of the purified products was used as a template for in vitro transcription using MEGAscript T7 transcription kit (Thermo Fisher Scientific). After the transcription reaction completed, RNA products were purified using RNAClean XP beads (Beckman Coulter) in a bead solution to sample ratio 3.0. The final gRNAs were quantified by Qubit RNS High Sensitivity kit (Thermo Fisher Scientific). The RNA reagent kit on a LabChip GX (Perkin-Elmer) was used to confirm the product size per the manufacturer's protocol.

Adapters for Library Prepraration:

Simplex and multiplex versions of adapters for the library preparation were used. For singleplex adapters, the top (5'-CGAGATCTACACTCTTTCCCTACACG-ACGCTCTTCCGATC*T-3' (SEQ ID NO:5)), which contains a phosphorothioate bond (indicated by *), and bottom (5'-/5Phos/GATCGGAAGAGCGTCGTG-TAGGGAAAGAGTGTAGATCTCG-3' (SEQ ID NO:6)) adapters were HPLC-purified (Integrated DNA Technologies). The multiplexed adapters contain a 7-base indexing sequence (NNNNNN*T) directly following the sequencing primer binding site (top: 5'-CGAGAT-CTACACTCTTTC-CCTACACGACGCTCTTCCGATC-TNNNNNN*T (SEQ ID NO:7); bottom: 5'-/5Phos/NNNNNNAGATCG-GAAGAGCGTCGTGTAGGGAAAGAGTGTAGATCTCG (SEQ ID NO:8)). Standard desalted ultramer oligonucleotides were used (Integrated DNA Technologies). Both simplex and multiplex adapters were annealed in a final concentration of 15 µM per adapter in Nuclease Free Duplex Buffer (IDT) by a 1% temperature ramp from 94° C. to 20° C., after an initial 5 min 94° C. denaturation step.

Targeted Fragmentation and Sequencing Library Preparation:

For each library, 500 ng or 1 µg gDNA was incubated in a 25-µl reaction mixture including 100 nM Cas9 nuclease, 1× reaction buffer (New England Biolabs), and 100 nM gRNA pool. The reaction was incubated at 37° C. overnight, and then heat-inactivated at 70° C. for 10 min. The fragmented DNA was purified using AMPure XP beads in a bead solution to sample ratio of 1.8 and used for the next step. The KAPA HyperPlus library preparation kit (KapaBiosystems) was used for the following steps. The gRNA-cleaved DNA was subject to random fragmentation with the KAPA enzyme mix; the incubation was at 37° C. for 9 min directly followed by incubation on ice. A-tailing enzyme mix was added to the final fragmentation products and the fragmented library was A-tailed with incubation at 65° C. for 30 min. Because the random fragmentation creates blunt-ended breaks, the end-repair step was omitted. The DNA ligase mix including 75 pmol annealed adapter and was added to the A-tailed library. The reaction volume was incubated at 20° C. for 15 min. Afterwards, the library products were purified with AMPure XP beads in a bead solution to sample ratio of 0.8. For the amplification-free preparation, the purified library was used directly for STR-Seq with no additional steps.

For those samples where PCR amplification of the sequencing libraries was used, several additional steps were included. 50-µl reactions for PCR amplification were prepared. The reaction mixture contained 25% volume of the adapter annealing step product, 1 µM amplification primer, 1× Kapa HiFi Hot Start Mastermix (KapaBiosystems, Woburn, Mass.). The amplification primer is the top strand of the singleplex adapter (Table 2). Reactions were denatured at 98° C. for 30 sec, followed by 11 cycles of 10 sec of 98° C., 30 sec of 65° C. and 30 sec of 72° C. The final steps involved an incubation at 72° C. for 7 min and cooling to 4° C. Amplified libraries were purified with AMPure XP beads in a bead solution to sample ratio of 1.0. For both PCR-free and PCR-amplified libraries, quantitative PCR was used to determine the concentration of the sequencing library. The 10-µl reaction included dilution of samples (1:10,000), 1 µM amplification primer, and 1× KAPA SYBR FAST qPCR Mastermix. The samples were denatured at 95° C. for 5 min, followed by 35 cycles of 30 sec of 95° C., 90 sec of 65° C. For absolute quantification, five serial 10th dilutions of 84.3 pM standard libraries were prepared and amplified with the sample libraries. The size distribution of the sequencing library was measured with the DNA High Sensitivity Reagent Kit on LabChip GX (Perkin-Elmer) per the manufacturer's protocol.

TABLE 2

Primers and Adapters

| ID | Description | Sequence |
| --- | --- | --- |
| ProbePool_F | Forward primer for amplification of array-synthesized primer probe pool | A*A*T*G*A*T*ACGGCGACGGATCAAGU (SEQ ID NO: 1) |
| ProbePool_R | Reverse primer for amplification of array-synthesized primer probe pool | /5Phos/CAAGCAGAAGACGGCATACGAGAT (SEQ ID NO: 2) |
| gRNApool_F_1 | Forward primers for amplification of array-synthesized guide RNA pool | GAGCTTCGGTTCACGCAATG (SEQ ID NO: 3) |
| gRNApool_F_2 |  | CAAGCAGAAGACGGCATACGAGAT (SEQ ID NO: 2) |
| gRNApool_R | Reverse primer for amplification of array-synthesized guide RNA pool | AAAGCACCGACTCGGTGCCACTTTTTCAAGT TGATAACGGACTAGCCTTATTTTAACTTGCT ATTTCTAGCTCTAAAAC (SEQ ID NO: 4) |
| Adapter_top; amplification primer | Top strand of singleplex adapter; primer for library amplification | CGAGATCTACACTCTTTCCCTACACGACGCT CTTCCGATC*T (SEQ ID NO: 5) |
| Adapter_bottom | Bottom strand of singleplex adapter | /5Phos/GATCGGAAGAGCGTCGTGTAGGGA AAGAGTGTAGATCTCG (SEQ ID NO: 6) |
| Adapter_M_top | Top strand of multiplex adapter | CGAGATCTACACTCTTTCCCTACACGACGCT CTTCCGATCTNNNNNN*T (SEQ ID NO: 7) |
| Adapter_M_bottom | Bottom strand of multiplex adapter | /5Phos/NNNNNNAGATCGGAAGAGCGTCGT GTAGGGAAAGAGTGTAGATCTCG (SEQ ID NO: 8) |

1) N*N: Phosphorothioate bond
2) /5Phos/: 5'phosphate motification
3) NNNNNN: sample index STR-Seq Assay:

The flowcell modification and capture assay procedures are as reported by Hopmans et al., *Nucleic Acids Research*, 42: e88, 2014. For preparing the targeting flow cell, a modified XML script for the Illumina cBot (Illumina, San Diego, Calif.) was generated as previously reported. The modification process requires (1) hybridization and extension of the target oligonucleotides onto the flow cell primer lawn and capturing of the sequencing library by overnight hybridization; (2) extension of the captured library and standard Illumina cluster generation.

Oligonucleotides and the sequencing library were heat denatured for 15 minutes at 95° C. followed by incubation on ice. Afterwards, both components were diluted with ice-cold 4× Hybridization buffer (20×SSC, 0.2% Tween-20) to a final total concentration of 50-100 nM for the primer probes and 150 ng/μl for the sequencing library. Denatured primer probes (100 μl) and libraries (30 μl) were loaded in separate 8 tube strips. A custom cBot reagent plate was created, containing hybridization buffer 1 (pos.1: HT1 or 5×SSC, 0.05% Tween-20), Extension mix (pos.2: 20U/ml Phusion (Thermo Scientific); 0.2 mM dNTP; 1× Phusion HF buffer), Wash buffer (pos.7: HT2 or 10 mM Tris buffer) and freshly prepared 0.1N NaOH (pos.10).

The reagent plate and eight-tube strips containing the denatured primer probes were loaded onto the Illumina cBot. "Wash before Run" and "Wash after Run" setting (i.e. Menu/Configure) were set to Optional. In the RunConfig.xml file, the number of cycles was increased to 42 (i.e. Amplification MaxNumCycles). Two different cBot programs were used for the subsequent steps (Hopmans et al., Nucleic Acids Research, 42: e88, 2014). The first cBot program (P1) automates the hybridization and extension of the primer probes to a subset of the P7 primers of the flow cell surface, followed by denaturation and removal of the original primer probe oligonucleotides. Finally, the denatured sequencing library is hybridized to the generated primer probe capture flow cell lawn in an overnight hybridization at 65° C.

After the completion of the P1 program, the second cBot program (P2) is started. When HiSeq High Output runs are performed, the standard Illumina cBot clustering reagent plate is used for this process. The P2 program for the High Output mode performs a stringency wash of the hybridized library, followed by the standard Illumina extension and clustering protocol. For HiSeq Rapid Run mode, another custom cBot reagent plate was created. The plate contains hybridization buffer 1 (pos.1: HT1 or 5×SSC, 0.05% Tween-20), Extension mix (pos.2: 20U/ml Phusion (Thermo Scientific); 0.2 mM dNTP; 1x Phusion HF buffer), Universal Sequencing Buffer (pos.3: USB), denaturing mix (pos.4: FDR), pre-amplification mix (pos.5: FPM), amplification mix (pos.6: AMS), Wash buffer (pos.7: HT2 or 10 mM Tris buffer) and freshly prepared 0.1N NaOH (pos.10). The P2 program for the Rapid Run mode performs a stringency wash of the hybridized library, followed by extension and initial five cycles of amplification. For runs performed using High Output mode, cBot clustering reagents and sequencing reagents (V3 for Illumina) for 101 cycle paired end reads were used. For runs performed using Rapid Run mode, v1 or v2 reagents were used for cBot sample loading, clustering, and sequencing (Illumina) for 2×150 cycle or 2×250 cycle paired end reads. For all the HiSeq experiments, image analysis and base calling were performed using the HCS 2.2.58 and RTA 1.18.64 software (Illumina). All sequence data has been deposited in the NIH Short Read Archive (SRP071335).

STR Genotyping:

Resource Files:

The following five data files describing the STRs and associated STR-Seq probes are required as input to the processing steps: i) str_probes.txt: containing STR-Seq probe number, genomic coordinates for probe alignment, name of targeted STR, and probe plus/minus orientation; ii) str_info.txt: containing STR name, repeat motif, STR genomic coordinates, minimum number of motif repeats required to consider the STR present in the region, and the 5' and 3' STR flanking sequences; iii) 5prflank.bed: containing STR name and 5' flanking sequence coordinates in .bed format; iv) 3prflank.bed: containing STR name and 3' flanking sequence coordinates in .bed format; v) noSTR_plus5b.bed: target bed coordinates for variant calling (excludes any STR motif regions). Selected STR metadata from these files is provided as data tables denoted as Assay1-STR and Assay2-STR. The complete files are available for download at "https:" followed by "//github." followed by "com/sgtc-stanford/STRSeq" in the Resources folder.

STR Indexing:

Single-end alignment to the NCBI v37 reference genome was performed on the sequencing reads using bwa-mem (Li and Durbin, *Bioinformatics*, 25: 1754-1760, 2009) v.0.7.4 with default parameters. For the paired end sequence, Read 1 is designed at R1 and Read 2 is designated as R2. Although it is not necessary to align the Read 1 to the genome, subsequent processing is facilitated by having both Read 1 and Read 2 sequencing reads in bam format. An indexing process was developed to analyze the R2 sam format alignment records and add a STR index tag. This involves adding a custom sam tag (ZP) to each read that aligns within 2 bases of an expected probe position. For example if the R2 read matched an expected alignment position for probe number 123, the tag 'ZP:i:123' would be added to the sequence read. Alignment position rather than the actual probe sequence is used in this step for determining the probe match thus delegating the mismatch tolerance to the alignment algorithm. R2 reads that do not match any expected probe position are discarded. The R1 mates of the remaining R2 reads are tagged with the same probe number as R2. This indexing method does not require R1 sequences to align to the genome; both aligned and unaligned reads are tagged based on alignment of their R2 mate to a designated primer probe sequence.

Motif Counting of Intact STRs in Sequence Reads:

The first step in evaluating reads for presence of an STR is to determine whether both the expected 5' and 3' STR flanking sequences are present in R1. The exact expected flanking sequences are available in the str_info.txt file described earlier. To allow for mismatches in the flanking sequences, FreeBayes (Garrison and Marth, *Preprint at arXiv*, 1207.3907v1202 [q-bio.GN], 2012) and vcftools (Danecek et al., *Bioinformatics*, 27: 2156-2158, 2011) were used to determine variant flanking sequences as follows: i) variants were called using FreeBayes v0.9.21-19 with the -noindels parameter; ii) bedtools intersectBed method was used to extract only the variants occurring in the 5' and 3' flanking regions described by the genomic coordinates in the 5prflank.bed and 3prflank.bed files; iii) a simple custom python script (str_flank_alleles.py) was used to exclude any complex variants and to reformat the variant file for further processing.

As described earlier, each R1 sequence read is tagged with the probe number to which its R2 mate aligned. Each probe number is associated with a targeted STR in the str_probes.txt file, and the str_info.txt file provides the expected 5' and 3' flanking sequences for each STR. Using this information, as well as any flanking sequence variants called by FreeBayes/bedtools, a custom python script (str_lengths_R1ref.py) is used to identify R1 reads that include the complete 5' and 3' flanking sequences and can therefore be expected to encompass the entire STR.

The next step in this process is to determine whether the expected STR motif repeat is present between the flanking sequences. The str_info.txt file specifies the expected motif, as well as a minimum number of STR motif repeats that should be present between the flanking sequences in order to consider the STR present. Thus for R1 reads which are identified as having an intact STR present, the read will comprise a 15 base 5' flanking sequence, followed by a variable length region containing at least a minimum number of STR motif repeats, followed by a 15 base 3' flanking region. For these reads STR motif repeat count is calculated by dividing the number of bases in the variable length region by the length of the STR motif. For example if the variable length region is 28 bases and the STR motif is GATA (tetramer), then the STR motif repeat count is 7.

Determining STR Alleles:

R1 reads encompassing entire STRs are counted, and summarized by motif repeat count to provide a basis for determining heterozygous vs homozygous STR alleles. For example, if all of the reads for a given STR have a motif repeat count of 7, then the STR allele is clearly homozygous. Stutter artifacts may be introduced during the PCR amplification process that results in a percentage of reads with STR motif repeat counts bracketing the true allele. The distribution of repeat counts and relative percentage of reads for each repeat count was used to differentiate heterozygous or homozygous STR alleles versus stutter artifacts. The major STR allele is determined by counting the sequence reads with a specific STR motif repeat. Other STR motif repeats are evaluated based on their repeat count distance from the major allele. For example, if the major STR allele has a motif repeat count of 10, and another allele has a repeat count of 8, the distance from the major allele is −2. Depending on the distance from the major allele, a candidate secondary allele must pass a read threshold for the STR to be considered heterozygous. The read thresholds as a fraction of the major allele reads are: 0.35, 0.15, 0.45, 0.02, corresponding to allelic distances of: −1, +1, <−1 and >+1 respectively. Details of how the thresholds were determined are outlined below.

Figure 7:
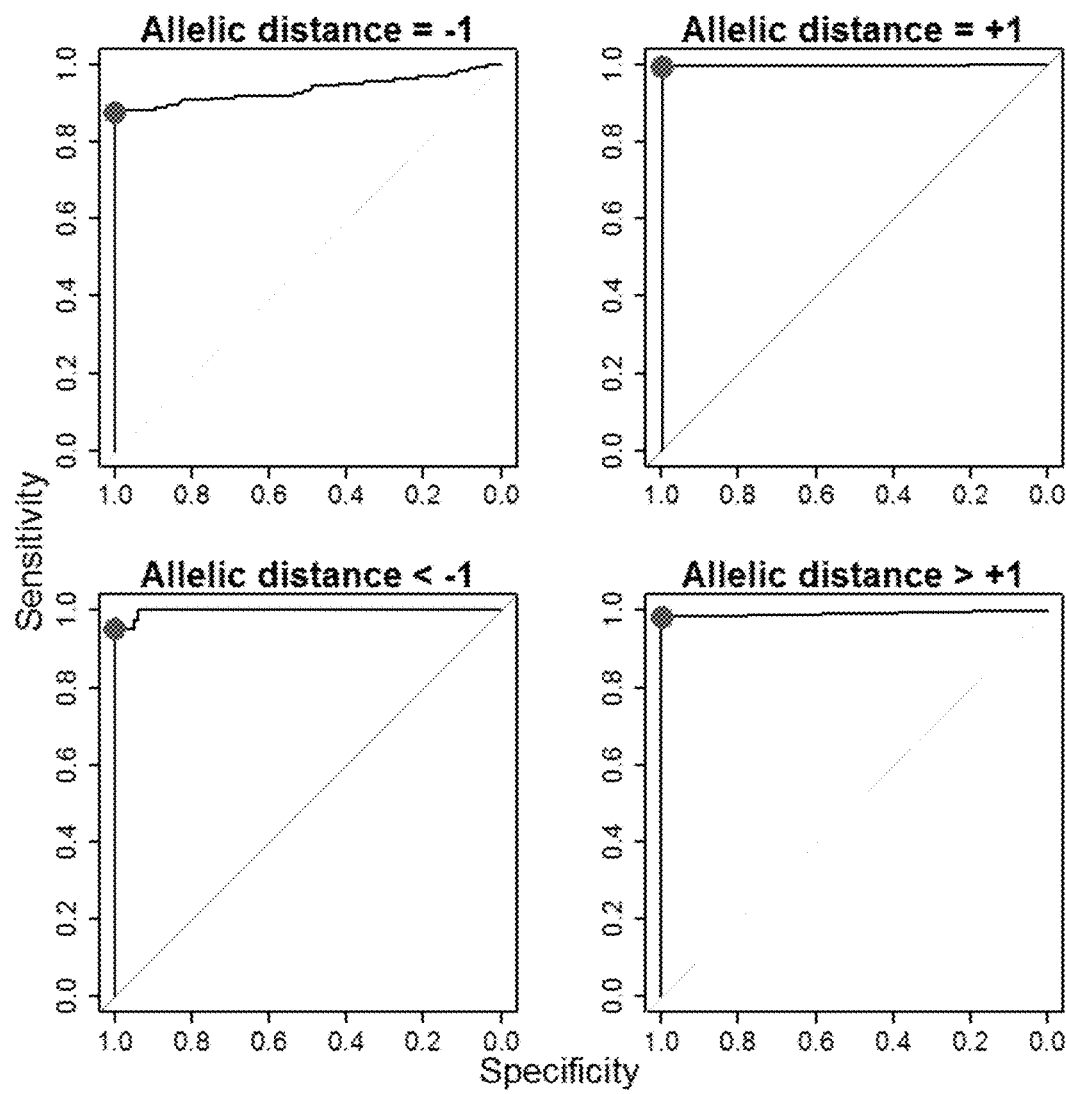
FIG. 7 shows receiver operating characteristic (ROC) curves created by specificity and sensitivity of thresholds for minor allele detection. Using the STR-Seq data from HGDP individuals having also been genotyped by CE, thresholds for four different allelic distances relative to the major allele (−1, +1, <−1 and >+1) were determined to maximize sensitivity of detection of secondary allele while maintaining the type II error below 0.01. The thresholds are respectively: 0.35, 0.15, 0.45, and 0.02 which are indicated as red dots on the curves.
Figure 8:
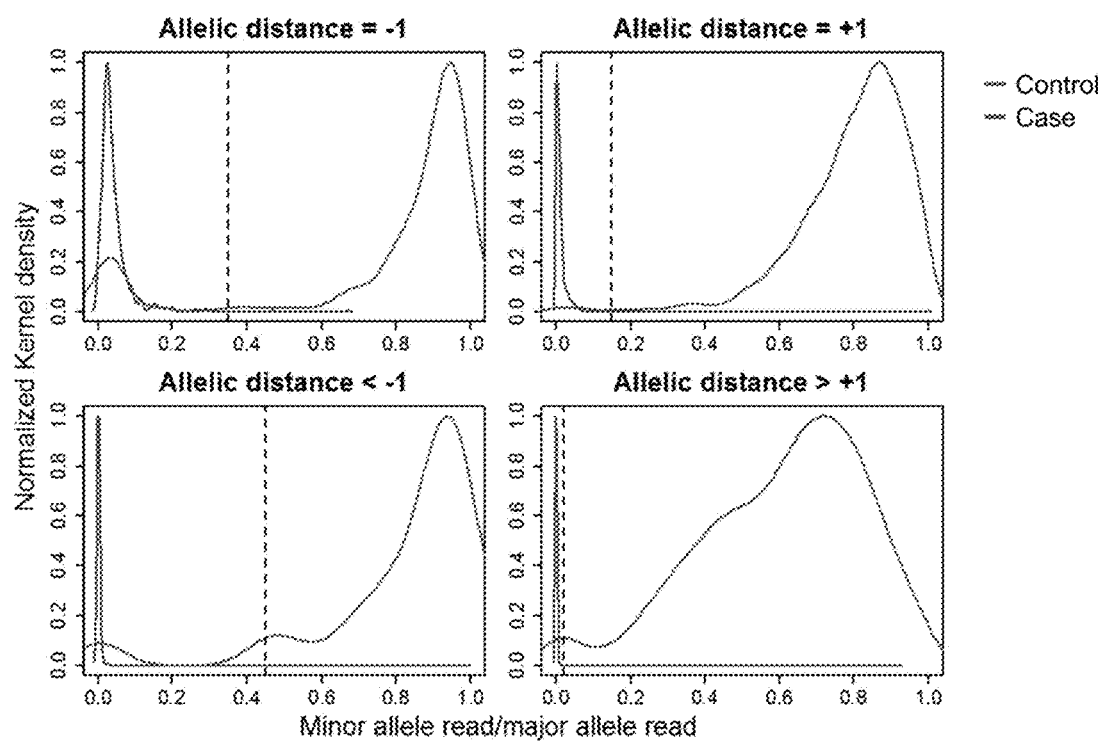
FIG. 8 shows the distribution ratio of minor allele read to major allele read. To test the null hypothesis (no secondary allele detection; i.e. homozygous call), a subset of the data having homozygous CE calls was used as controls. Distribution of number of reads having the same allelic distance from the major allele showed generally a good separation between the case and control. Dotted vertical lines indicate the thresholds used to differentiate an allele from noise. The estimated Kernel density is normalized for easier comparison.

Threshold Determination per Allelic Distance:

Using the STR-Seq data from HGDP individuals having also been genotyped by CE, thresholds for four different allelic distances relative to the major allele (−1, +1, <−1 and >+1) were determined to maximize sensitivity of detection of secondary allele while maintaining the type II error below 0.01. FIG. 7 shows receiver operating characteristic (ROC) curves for all the categories, in which the determined thresholds were indicated. The thresholds are as follows: 0.35, 0.15, 0.45, 0.02 which reflects the finding that PCR amplification induced stutter is more likely occurs as a deletion of a motif than insertion, and additionally that longer motif repeats will more often be impacted by sequencing read length being insufficient to capture the entire STR region plus flanking sequences. To test the null hypothesis (no secondary allele detection; i.e. homozygous call), a subset of the data having homozygous CE calls was used as controls. Distribution of number of reads having the same allelic distance from the major allele showed generally a good separation between the case and control (FIG. 8).

Comparison with CE Microsatellite Genotypes:

When comparing STR-Seq with CE, many STRs demonstrated a consistent offset of one or more repeat units. This may be due to annotation differences. First, the start and end positions of STRs can vary because those were adjusted to ensure the flanking sequences were unique and free of high frequency SNPs in each targeted region. Second, some CE annotations include multiple STRs separated by non-repetitive sequences, for which STR-Seq targeted only the longest. Therefore, prior to comparing genotypes, the median of all the offsets for every locus was calculated and used to compare CE versus STR-Seq calls.

STR-SNP Haplotypes:

SNP Calling:

The bamUtil ("http:" followed by "//genome.sph.umich." followed by "edu/wiki/BamUtil") v0.1.13 trimBam method was used to mask the first 40 bases of R2 reads in the forward orientation, and the last 40 bases of R2 reads in the reverse orientation. This masking is performed so that the synthetic probe DNA which by design matches the reference sequence, does not influence the variant discovery. FreeBayes v0.9.21-19 with quality and coverage filters was used to call R2 variants. The parameters used are: —pvar 0.05, —no-mnps, —no-complex, —min-mapping-quality 25, —min-base-quality 15, —min-coverage 3, —min-supporting-mapping-qsum 90, —min-supporting-allele-qsum 60. The coverage, mapping and base quality parameters were chosen to minimize type I errors when comparing NA12878 variant calls to the Illumina platinum genomes ("http:" followed by "//www.illumina." followed by "com/platinumgenomes") calls for the same sample (see Methods, SNP validation). Vcftools (Danecek et al., *Bioinformatics*, 27: 2156-2158, 2011) v0.1.11 was then used to exclude variant calls in any locus that encompasses an STR repeat. This step may be necessary because some STRs are in close proximity to each other and especially with longer read lengths, the R2 read targeting one STR could include all or part of a repeat region for a different STR. Due to the inherent variability in these regions relative to the genome reference, it is not informative to consider these variants in STR-SNP phasing. This filtering is accomplished by providing a .bed file (noSTR_plus5b.bed) that excludes these STR repeat regions, to the vcftools step. Additionally in the vcftools filtering step, any SNPs which are within 6 bp of each other are removed, as are indels or variants which do not have a status of 'PASS' from FreeBayes. Parameters used are: —thin 6, —remove-indels, —remove-filtered-all, and -bed. As a final quality filtering step, vcffilter ("https:" followed by "//github." Followed by "com/vcflib/vcflib#vcflib") is used to include only those reads with average alternate base quality>8 (QUAL/AO>8).

Phasing STRs with SNPs for Haplotypes:

Picard ("http:" followed by //broadinstitute.github." followed by "io/picard/") v1.97 FilterSamReads method with FILTER—includeReadList parameter was used to select only R2 alignment sequences that paired with R1 sequences having intact microsatellites. Of those R2 alignment sequences, only the ones that cover one or more of the SNP positions determined in the previous section are extracted using a python script (pstr_extract_R2SNP.py). In this step, additional filtering is also performed to exclude any R2 reads for which the base at the SNP position is either not a reference or alternate allele as reported by FreeBayes, or if FreeBayes reports the allele frequency as 0. For example if the reference base frequency is 0 and alternate base frequency is 1, only the reads with the alternate base will continue to the next step. The resulting R2 sequences are merged with the STR metadata derived from the R1 mate sequence (pstr_merge_str_sny.py). Subsequently, the python script (pstr_genotyping.py) summarizes the read counts in the merged file by STR, SNP allele and STR motif repeat count. Finally, the script (pstr_haplotype_cts.py) is used to make the haplotype calls. For homozygous SNPs, the STR-SNP haplotypes are determined by evaluating allelic difference and read count thresholds as in the STR genotyping. If no STR allele passes the threshold test, the STR-SNP haplotype will be homozygous (eg. A-11), otherwise it will be heterozygous, (eg A-11, A-13). For heterozygous SNPs the STR-SNP haplotype will be heterozygous—formed by associating each SNP base with its major STR repeat allele, simply by majority counting (eg A-11, C-13).

SNP Analysis and Validation:

To confirm the validity of the SNP calls, SNPs derived from the high coverage whole genome sequencing of the HapMap sample NA12878 were used as a ground truth set. This sample was subject to Illumina-sequencing at an average coverage of 200× on a HiSeq 2000 system, using an amplification free library. The platinum genomes vcf file was downloaded from Illumina and filtered with vcftools using the following filters: —thin 6 —remove-filtered-all —remove-indels —recode —recode-INFO-all, and with —bed file filtering using the noSTR_plus5b.bed file for either Assay 1 or Assay 2, depending on the comparison being performed. The same filters were applied to the NA12878 vcf files generated by Assay 1 and Assay 2. Vcftools was then run with the -diff and -diff-sites parameters to compare the two vcf files. The STR-Seq vcf calls were tested with a combination of parameters: min-coverage=3, 5, 8 or 10, min-base-quality=10, 15 or 20, min-mapping-quality=25 or 30. The parameters determined to minimize false positive SNP calls were the lower to mid end of the parameters tested: min-coverage=3, min-base-quality=15, min-mapping-quality=25. Additionally to require slightly higher base and mapping quality for low coverage STRs, the following parameters were also used: min-supporting-mapping-qsum=30×min-coverage=90, and min-supporting-allele-qsum=20×min-coverage=60. This further reduced the putative false positive calls to 0 of 135 SNP calls for Assay 1, and 212 of 1535 SNP calls for Assay 2.

Validation of Haplotypes:

To determine the accuracy of phased STR-SNP haplotypes, the Mendelian inheritance patterns of a family trio were evaluated (NA12878-daughter, NA12891-father, and NA12892-mother). The standard STR-Seq genotyping and haplotyping pipeline was first run for all three members of the trio. Next, the parents were assessed for the presence of variants found in the child. The process documented in the Phasing STRs with SNPs method section (pstr_extract_R2snv.py, pstr_merge_str_snv.py, pstr_genotyping.py, pstr_haplotype_cts.py) was rerun, using the variant calls for the child, in place of the parent variant calls. The parent was considered heterozygous for the reference and variant if the secondary allele comprises at least 15% of the reads at that position. Though a heterozygous allele should theoretically be 50% of the reads, if the SNP is phased with a longer STR allele, there will be a greater number of reads that truncate the STR region. Stutter in the simpler repeat motifs will distribute the read counts over a greater number of phased haplotypes. Once the parental haplotypes are called, the parent and child haplotype files are merged and compared to determine if the child haplotype can be explained by Mendelian inheritance of one phased allele from each parent. Final concordance percentages are based on coverage of at least 10 reads at a given SNP position, for each member of the trio.

The STR genotyping was run with scripts developed using the bioinformatics pipeline tool bpipe (Sadedin et al., Bioinformatics, 28: 1525-1526, 2012). All software and resource files used in STR-Seq, including the bpipe pipeline, a shell script alternative, and the python scripts referenced in methods, are available at: "https:" followed by "//github." followed by "com/sgtc-stanford/STRSeq".

Example 1

Overview of STR-Seq

Figure 9:
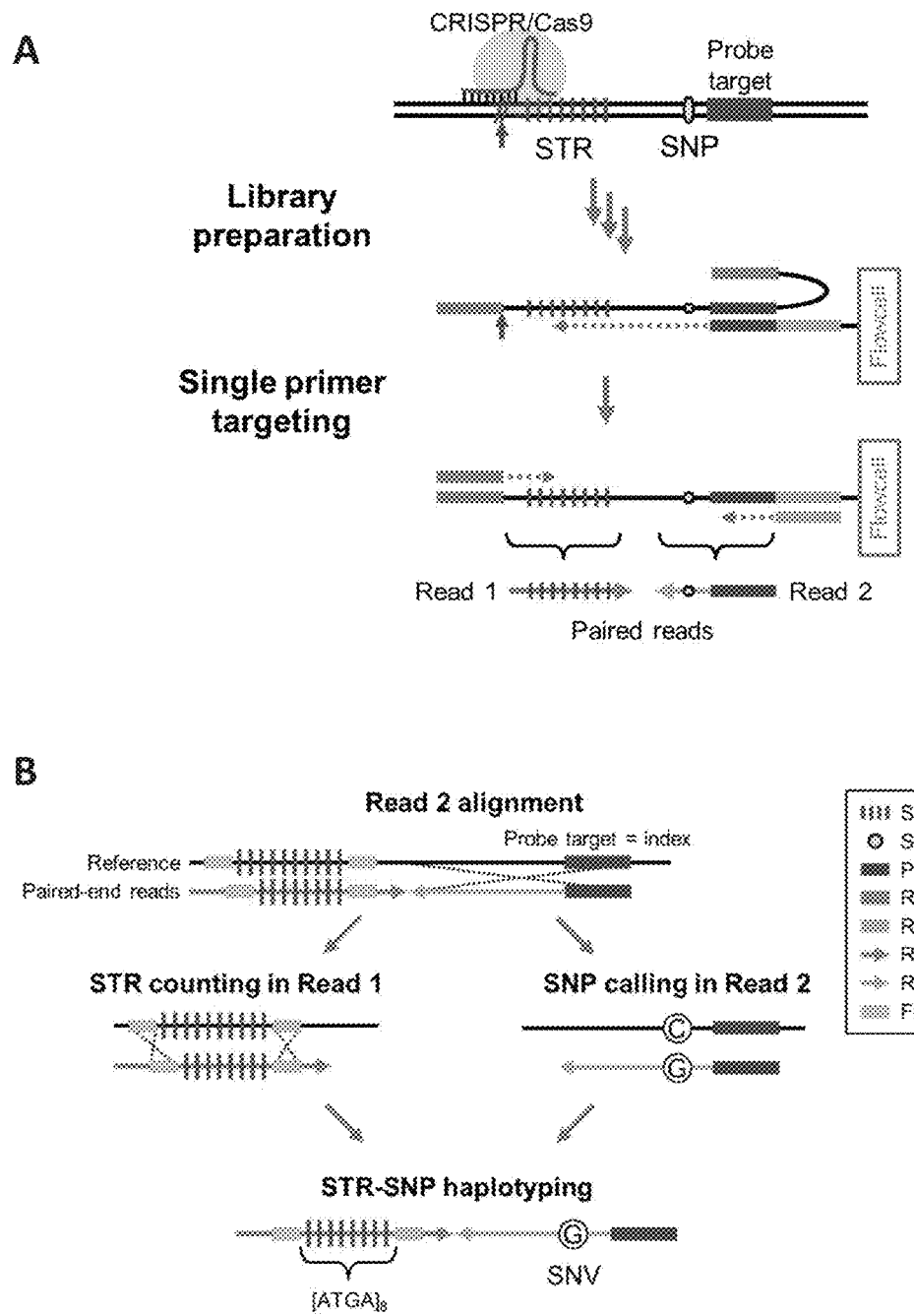
FIG. 9 shows an overview of STR-Seq. 9A: Guide RNAs and primer probes were designed to target STRs and proximal SNPs. Both plus and minus strands were targeted with only the plus strand targeting is illustrated. In the first step, Cas9 enzyme cleaves upstream of STR. The DNA libraries including the STR and SNP are target sequenced. 9B: After initial alignment of Read 2 from any given paired-end set, the primer probe sequence derived from Read 2 was use as an index tag to link the Read 1 microsatellite internal motif and flanking sequences. STR genotypes are called from Read 1. SNPs are phased with the STR genotype to generate haplotypes. 9C: As an example of STR-Seq haplotyping, paired end alignments to the reference genome are shown for an STR target (trf747130) for sample NA12878. After the STR genotyping process, 114 and 133 read pairs were identified to have 11 and 8 repeats of a tetranucleotide motif (ATGA) in their Read 1 s, respectively. Within each read pair group, all the base calls at the SNP position were identical, being either C (reference) or G (alternative). The site where Cas9/CRISPR targets is indicated with red arrow, and the two haplotypes are illustrated on the bottom.
Figure 9:
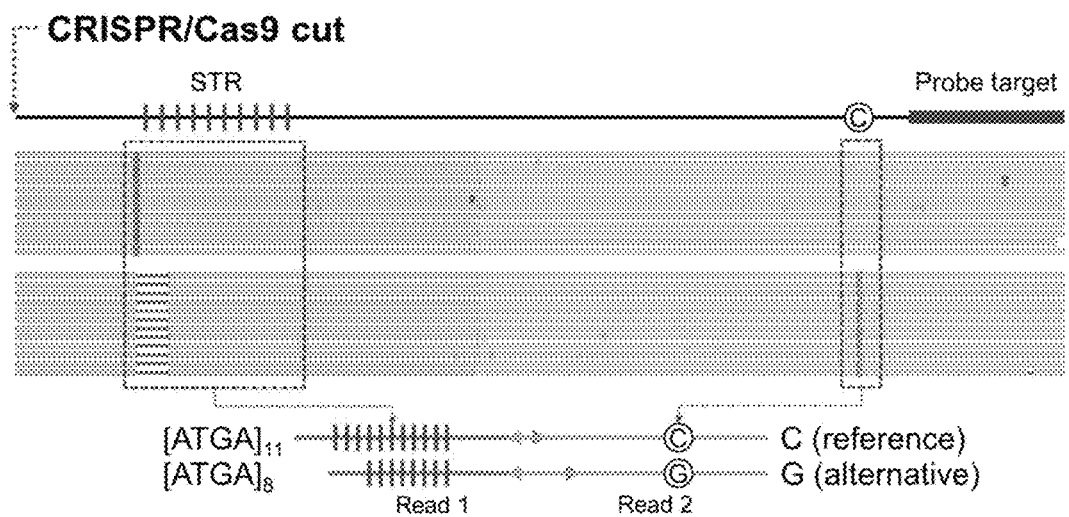
Figure 10:
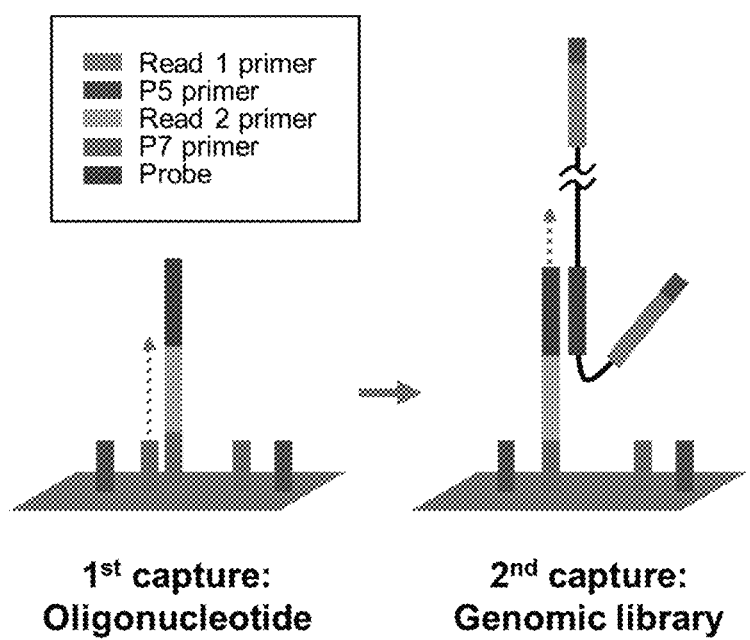
FIG. 10 shows an embodiment of single primer targeting on an Illumina flowcell. The single primer targeting involves two captures: one is for modification of Illumina flowcell surface, and other for genomic library capture. First, oligonucleotide including the probe was hybridized, Read 2 sequencing primer, and P7 primer as the parts. The extension from P7 on the flowcell results in immobilized primer probes. Second, the genomic libraries including the probe target sequences are hybridized to the primer probes, and the capture is completed by extension from the primer probes.

FIG. 9A provides an overview of genomic selection process of STR-Seq. Sequencing libraries are generated from either random or targeted DNA fragmentation. In the latter case, CRISPR/Cas9 guide RNAs (gRNAs) were designed and synthesized to selectively cut genomic DNA sites flanking a target STR loci. Afterwards, a single-adapter library was generated. STR-Seq uses 40-mer sequences called primer probes, that mediate STR targeting and are directly incorporated into the Illumina flow cell. As the next step, the sequencing library is introduced into the modified flow cell. The primer probes anneal to target DNA fragments for a given STR locus (FIG. 10) and primer extension incorporate the microsatellite sequence. Sequencing produces paired end reads, referred to as Reads 1 and 2. The original primer probe sequence (i.e. a STR index) was extracted from Read 2 to assign the paired Read 1 to a specific STR locus. This bioinformatic process minimizes the need for sequence alignment to repetitive regions, reduces the contribution of off-target effects and improves genotyping accuracy. STR-Seq utilizes an indexing process with the paired sequences where Read 2 includes the targeting primer sequence (i.e. STR index) and Read 1 spans an entire STR region. Because every Read 2 starts with a targeting primer sequence, coverage for SNP regions is high and ensures accurate genotypes. All sequence data has been deposited in the NIH Short Read Archive (SRP071335).

Example 2

Designing and Generating STR-Seq Assays

Figure 11:
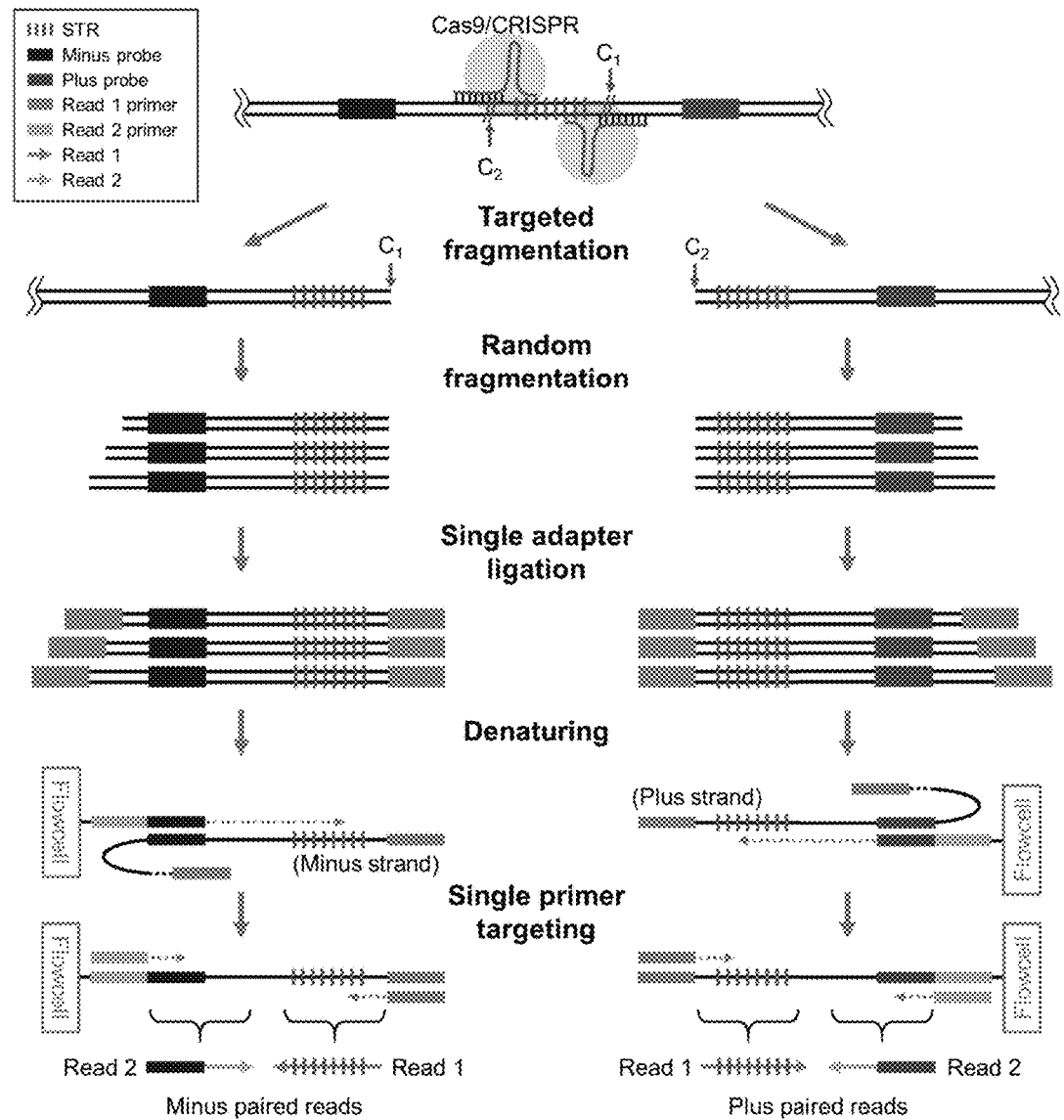
FIG. 11 shows an embodiment of the STR-Seq genomic selection process for both double strands. To target both strands of fragments including STR information, two separate reaction and sequencing processes were performed from portions of sample (e.g., a portion for capturing the plus strand, and the remaining portion for the minus strand). Guide RNAs were designed to complementarily bind and cleave upstream or downstream of STRs. These gRNAs are paired with probes which capture the STR from the opposite side where the targeted fragmentation occurs. For example, if a gRNA cleaves downstream of a STR (indicated as C1), a probe captures the cleaved fragment from upstream (indicated as minus probe). After targeted fragmentation by in vitro reaction with Cas9/gRNA complexes, the target-specifically cleaved product is randomly fragmented to get a mean fragment size of 500 bp which is optimal for following target capture process. Following the random fragmentation, an adapter including the Read 1 primer sequence is ligated for both the ends of the fragments. The ligated product can be further amplified using primers binding the adapter sequence or be directly used for the next target capture step. After denaturing the double-stranded libraries, plus and minus strands are captured respectively over two sequencing lanes; each sequencing lane has immobilized primer probes only targeting either of the two strands. The capture involves target library hybridization and extension to result in immobilized targets ready to be sequenced. For both the strand captures, the STR sequence is derived from Read 1 and the primer probe sequence from Read 2 sequencing reads. Direction of sequencing is different depending on the strandness; i.e., Read 1 from the plus strand aligns to the reference genome itself while Read 1 from the minus strand aligns to the reverse complementary.

The locations of over 740,000 tandem repeats were obtained from the UCSC Genome Browser. Known STRs with documented polymorphisms and candidate STRs not previously reported to be polymorphic were identified. The selection of STRs was limited to those that could be covered in their entirety within a 150 bp read. To increase the number of potential STR-SNP haplotypes, tandem repeats that were within 100 bp of a SNP with a high genotype frequency among different populations were identified. The analysis identified a total of 10,090 tandem repeat loci that fulfilled the targeting criteria and were in proximity to a SNP position. Afterwards, candidate primers were identified based on their uniqueness in the human genome reference, requiring at least two edited bases to align in any other location. Targeting primers were positioned on opposing strands (FIG. 11); this double strand coverage was particularly useful because a true STR variant should be the same for both the forward and reverse strand reads.

Two STR-Seq assays were developed (Table 1). Assay 1 was designed to sequence 700 STRs that included 491 microsatellites with CE genotypes from a set of well characterized DNA samples. These samples and their CE-based genotypes provided a ground truth data set to assess the accuracy of STR-Seq's genotyping. Assay 2 targeted 2,370 loci for which 964 STRs fulfilled the criteria as microsatellites per Willems et al., *Genome Research,* 24: 1894-1904, 2014, while the remaining 1,406 were candidate STRs or homopolymers. Each assay had a number of control non-microsatellite targets. A subset of primer probes targeting 2,191 STRs with reported SNP positions within 100 bp of the probe. Array-synthesized oligonucleotides were used for Assay 2 (see, Materials and Methods; FIG. 5).

Example 3

STR-Seq Genotype and Haplotype Calling

To genotype STRs while avoiding alignment artifacts (i.e. soft clips) that arbitrarily truncate the microsatellite sequence, the synthetic primer probe sequence in Read 2 was used to generate an STR index tag (see, Materials and Methods; FIG. 9B). If the primer probe sequence aligns within 2 bp of the expected primer probe start position, the paired Read 1 was assigned to its specific STR index tag. Using this process, indexed STR counts per sample ranged from 0.6 to 58 million reads depending on the experiment and degree of sample multiplexing (Table 3).

TABLE 3

STR-Seq Sequence Data Summary

| Assay | Sample | Description | | STR-Indexed Reads | STR-Spanning Reads |
|---|---|---|---|---|---|
| 1 | HGDP00932 | Comparison with CE and WGS/lobSTR | | 7,232,518 | 1,185,602 |
| | HGDP01414 | | | 7,290,935 | 1,035,335 |
| | HGDP01032 | | | 6,573,815 | 857,650 |
| | HGDP01034 | | | 6,018,727 | 882,646 |
| | HGDP01035 | | | 5,965,471 | 686,093 |
| | HGDP01417 | | | 6,317,790 | 1,054,932 |
| | HGDP00457 | | | 8,888,780 | 1,457,616 |
| | HGDP01028 | | | 6,518,411 | 1,065,862 |
| | HGDP01030 | | | 5,243,927 | 776,696 |
| | NA12878 | Trio validation | Child | 6,857,135 | 1,073,854 |
| | NA12892 | | Mother | 6,153,251 | 885,897 |
| | NA12891 | | Father | 7,207,190 | 1,161,060 |
| | NA12878 | PCR-free library | | 15,449,065 | 2,887,433 |
| | HGDP00474 | Cas9/gRNA protocol test | Negative control | 1,036,847 | 67,266 |
| | | | Before shear | 617,811 | 45,927 |
| | | | After shear | 715,060 | 47,836 |
| | | | After ligation | 728,691 | 47,004 |
| | NA12878 | Cas9/g RNA test | Test | 27,892,582 | 4,031,145 |
| | | | Negative control | 6,372,609 | 405,739 |
| | HGDP00924 | HGDP 2-component mixture | 100% | 10,509,382 | 603,047 |
| | HGDP00924 + HGDP00925 | | 25% | 9,952,520 | 583,935 |
| | | | 10% | 9,965,431 | 575,352 |
| | | | 5% | 14,251,933 | 832,042 |
| | | | 1% | 50,487,512 | 3,354,830 |
| | | | 0.5% | 57,506,545 | 3,774,898 |
| | | | 0.1% | 48,755,553 | 3,208,061 |
| | HGDP00924 + 5 HGDP samples | HGDP 6-component mixture | 25% | 9,632,303 | 545,661 |
| | | | 10% | 9,015,013 | 516,386 |
| | | | 5% | 13,295,252 | 786,984 |
| | | | 1% | 50,985,639 | 3,289,170 |
| | | | 0.50% | 46,663,163 | 3,067,503 |
| | | | 0.10% | 44,780,708 | 2,882,769 |
| 2 | NA12878 | Trio validation | Child | 2,771,248 | 311,064 |
| | NA12892 | | Mother | 2,965,677 | 371,068 |
| | NA12891 | | Father | 3,177,145 | 408,969 |
| | NA12892 | HapMap 2-component mixture | 100% | 1,409,834 | 180,751 |
| | NA12891 | | 100% | 1,942,307 | 292,390 |
| | NA12892(minor) + NA12891 | | 40% | 1,361,063 | 209,455 |
| | | | 20% | 2,092,649 | 300,972 |
| | | | 5% | 1,857,072 | 287,201 |
| | | | 1% | 999,480 | 156,450 |

Microsatellite genotypes are quantitative and reported as the number of motif repeats. After assigning an STR index tag to each paired-end read, the Read 1 sequence was evaluated for the presence of the expected STR (see, Materials and Methods; FIG. 9B; Table 3). Based on the human genome reference, the flanking genomic sequences that mark the complete STR segment were identified, and then the composition (i.e. mononucleotide, dinucleotide, etc.) and overall length of the repeat motif structure was determined. Read 1 sequences that contained both the 5' and 3' flanking sequences with the internal microsatellite were used for genotyping.

STR allele sizes were calculated by dividing the microsatellite length by the number of bases in the individual motif. Subsequently, a statistical model threshold to identify valid genotypes was applied (see, Materials and Methods). For STR-SNP haplotypes, FreeBayes (Garrison and Marth, *Preprint at arXiv*, 1207.3907v1202 [q-bio.GN], 2012) was used for SNP calling on the remaining Read 2 sequence not containing the primer probe. Haplotypes were generated by combining the STR genotype originating from Read 1, with the SNPs from the Read 2 sequences (FIG. 9C).

Example 4

Validating STR-Seq Genotypes

To validate STR-Seq's genotyping accuracy, Assay 1 was used to sequence nine genomic DNA samples with 470 CE-based genotypes. These samples also had STR genotypes derived from WGS with the program lobSTR (Willems et al., Genome Research, 24: 1894-1904, 2014). To compare genotypes among the different methods, a dosage value that is derived from the number of base pairs remaining after subtracting the reference allele was used. For example, an STR locus with a reference size of 18 bp and heterozygous STR alleles of 16 bp and 24 bp would have an STR dosage of −2+6=4.

Among the nine samples, STR-Seq analysis produced 439 to 464 STRs (Table 4) that overlapped with the CE-derived genotypes. Each sample demonstrated greater than 94% concordance where STR-Seq genotypes agreed with the CE genotypes. Considering all nine samples in total, 95.51% of 4,119 STRs per STR-Seq were concordant with CE. STR-Seq accuracy was confirmed by a high correlation between CE and STR-Seq genotype dosage (FIG. 12A; $R^2$=0.98). Among a subset of 191 discordant STRs, the correlation of genotype dosage was still significant ($R^2$=0.75, p<2.2e-16). These discordant STR genotypes arose from microsatellites that exceeded the sequence read length or originated from STRs with indels in the flanking sequences.

The genotype concordance was compared among the subset of STRs called by all three methods (CE, STR-Seq and WGS/lobSTR). This ranged from 266 to 293 STRs per sample. The lower number of STRs was a result of the WGS method identifying only a fraction of the CE genotypes (up to 464 STRs), thus representing a category of WGS false negatives. On this overlapping subset, STR-Seq genotypes were 97.83% concordant with CE while WGS/lobSTR genotypes were 94.00% concordant with CE (Table 4). STR-Seq genotypes were equally accurate whether they were heterozygous or homozygous. STR-Seq and CE genotypes showed a higher concordance for heterozygotes with alleles had a greater difference in repeat number. WGS/lobSTR genotypes had a lower CE concordance for homozygous alleles compared to STR-Seq.

As another method for determining genotype accuracy, samples from a family trio were analyzed (NA12878—female child, NA12891—father and NA12892—mother). Specifically, it was determined whether the paternal and maternal alleles were identified in the child per parental inheritance. 679 STRs were identified from Assay 1 and 1,617 STRs were identified from Assay 2 where genotypes were available from all three family members. When evaluating the child's STRs with Assay 1, 98.50% of the genotypes were concordant with paternal and maternal inheritance (Table 5). With Assay 2, the child's genotypes demonstrated 96.29% concordance in terms of paternal and maternal inheritance.

TABLE 5

STR-Seq Trio Validation

| Assay | Type | NA12878 (Child) | Genotype available from both parents | Mendelian |
|---|---|---|---|---|
| 1 | STR | 686 | 679 | 98.50% |
|  | SNV | 143 | 143 | 97.90% |
|  | STR-SNV | 132 | 128 | 97.66% |

TABLE 4

STR-Seq Comparison with Capillary Electrophoresis (CE) Genotypes

| Sample | Comparison with CE ground truth genotypes (N = 470) | | Comparison with CE ground truth genotypes (N = 470) | Concordance of CE genotype with WGS subset | |
|---|---|---|---|---|---|
|  | STR-Seq genotypes | Concordance with CE genotypes | WGS genotypes | STR-Seq genotypes | WGS genotypes |
| HGDP00932 | 459 | 95.86% | 267 | 97.00% | 92.13% |
| HGDP01414 | 439 | 96.36% | 284 | 98.59% | 94.01% |
| HGDP01032 | 463 | 95.90% | 271 | 97.79% | 94.83% |
| HGDP01034 | 464 | 95.69% | 292 | 96.92% | 94.18% |
| HGDP01035 | 461 | 95.23% | 284 | 98.24% | 96.13% |
| HGDP01417 | 457 | 95.40% | 291 | 97.94% | 94.50% |
| HGDP00457 | 461 | 94.58% | 285 | 97.54% | 92.98% |
| HGDP01028 | 452 | 94.91% | 293 | 97.27% | 92.15% |
| HGDP01030 | 463 | 95.68% | 266 | 99.25% | 95.11% |
| Total | 4119 | 95.51% | 2533 | 97.83% | 94.00% |
| Total homozygous | 953 | 96.54% | 567 | 97.88% | 88.71% |
| Total heterozygous | 3166 | 95.20% | 1966 | 97.81% | 95.52% |

TABLE 5-continued

STR-Seq Trio Validation

| Assay | Type | NA12878 (Child) | Genotype available from both parents | Mendelian |
|---|---|---|---|---|
| 2 | STR | 1,848 | 1,617 | 96.29% |
|   | SNV | 2,447 | 2,430 | 95.80% |
|   | SIR-SNV | 1,499 | 1,324 | 93.88% |

With this family trio, the accuracy of SNPs called from STR-Seq was verified. With Assay 1 a total of 143 SNPs were identified present among all three family members (Table 5). From these SNPs, 97.90% of the child SNP genotypes were concordant with parental inheritance. In addition, 139 of the SNPs matched those genotypes previously reported from WGS analysis of this trio. For the remaining SNPs not reported from WGS, four showed Mendelian inheritance from the parents, and two were registered SNPs in dbSNP. It is likely that these non-reported SNPs were false negatives from the WGS analysis.

Assay 2 generated 2,430 SNPs of which 95.80% of the child SNP genotypes were concordant with parental inheritance. From this set, 1,994 SNPs were previously reported per WGS analysis. Among the remaining 436 SNPs that were not reported, 382 demonstrated maternal/paternal inheritance to the child, and 387 were reported in dbSNP. Many of these SNPS that were not called form the WGS analysis of the child represent potential false negatives.

To determine the accuracy of STR-SNP haplotypes, the results from the family trio sequencing was used and haplotypes were determined by phasing those SNPs with STR genotypes. For Assay 1, 128 informative haplotypes were identified among all three family members. For the child's STR-SNP haplotypes, 97.66% were concordant with parental inheritance. For Assay 2, 1,324 haplotypes were identified in the family trio. For the child STR-SNP haplotypes, 93.88% demonstrated parental inheritance. The majority of the STR-SNP haplotypes not concordant with paternal or maternal segregation originated from STRs located in highly repetitive segments of the genome. These highly repetitive regions are difficult to target and this factor likely caused the discordant genotypes.

Example 5

Amplification-free STR-Seq Reduces Sequence Artifacts

Figure 12:
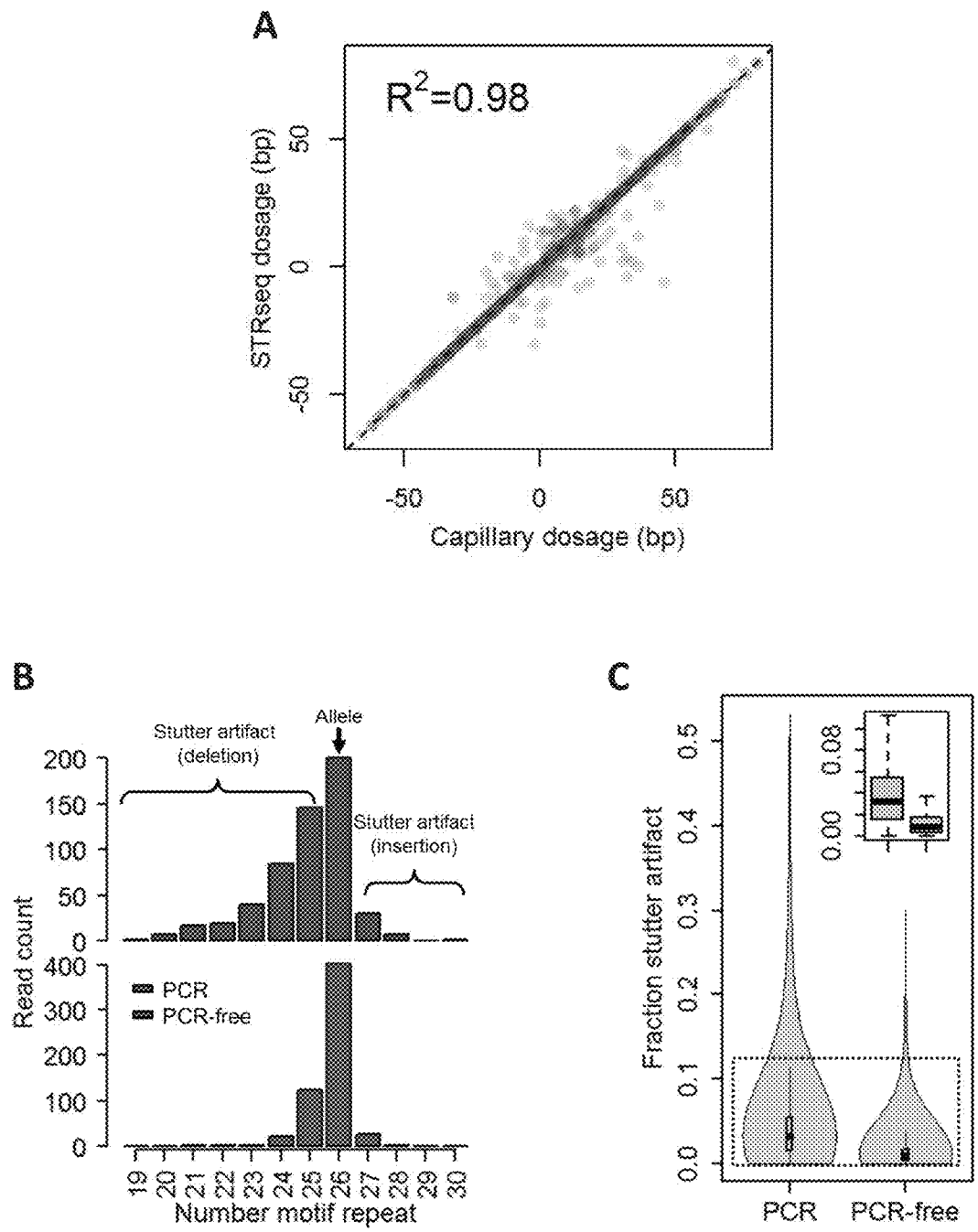
FIG. 12 shows the performance of STR-Seq. 12A: The STR alleles determined by STR-Seq and CE are compared using a 'dosage' value that is derived from the number of base pairs remaining after subtracting the reference allele. The R-squared value is shown at the top left in the plot, and the dotted diagonal line indicates 1:1 concordance. 12B: BAT26 is an example where the true STR allele was obscured by artificial indels. The bar graphs show read counts for all observed alleles both for PCR-amplified (blue) and PCR-free (red) STR-Seq analyses. PCR-free STR-Seq analysis reduced the fraction of stutter artifact from 64% to 30%. The STR allelotype is indicated by number of motif repeats, and the true allelotype is indicated with the black arrow on the top of the corresponding bar. 12C: The distributions of stutter artifact fractions are shown for NA12878's 686 STRs. For each STR, number of non-allelic reads is divided by the total number STR-spanning reads to get the fraction of artificial indels. Box plots for PCR-amplified (left) versus PCR-free (right) are shown top right. The horizontal thickness represents estimated and normalized Kernel density.
Figure 13:
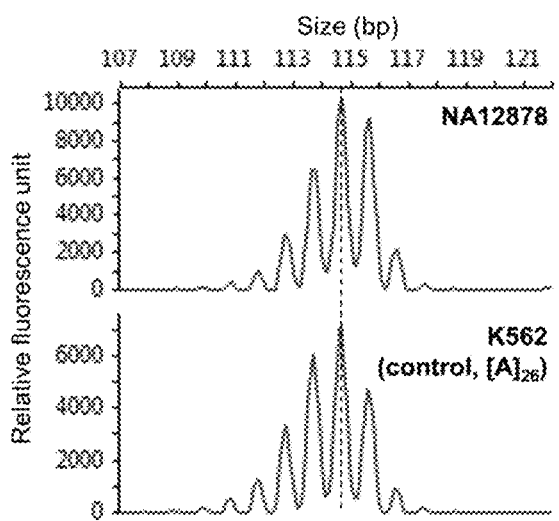
FIG. 13 shows capillary electrophoresis validation of BAT26 phenotype. To validate genotype of BAT26 from STR-Seq, capillary electrophoresis (CE) was performed using the sample gDNA (NA12878) as well as a control gDNA (K562) with known BAT26 genotype. MSI Analysis System v1.2 (Promega, Madison, Wis.) was used to generate amplified and fluorescence-labeled fragments ready for CE analysis. Electropherograms show both fragment profiles from NA12878 (top) and K562 (bottom). The profiles including peaks for artificial indels match each other, suggesting the genotype of NA12878 is [A]26 which is same with that of K562. X- and y-axes indicate size of DNA fragment and relative fluorescence unit, respectively. Peak Scanner Software v2.0 (Thermo Fisher Scientific, Waltham, Mass.) was used for sizing the fragments; for example, the size of highest peak from both sample and control was determined to be approximately 115 bp (dotted line).

To reduce PCR artifacts in microsatellites, a PCR-free method for library preparation was developed. NA12878 was sequenced with Assay 1, using either PCR-amplified or PCR-free sequencing libraries and genotyping results were compared among 686 STRs (Table 6). Citing an example of the effects of amplification-free library preparation, the microsatellite BAT26 that is composed of 26 mononucleotide (A) repeats was examined (FIG. 13). From the PCR-amplified libraries, STR-Seq analysis generated BAT26 motif repeats ranging from 19 to 30; all of these variations were attributable to stutter artifacts (FIG. 12B). With the PCR-free method, the true BAT26 allelotype was apparent without significant stutter.

TABLE 6

STR-Seq Genotyping Summary

| Assay | Description | Sample | Genotyped STRs | Homozygous STR genotypes | Heterozygous STR genotypes | Homozygous STR-SNP haplotypes | Heterozygous STR-SNP haplotypes | Total phased STR | Total phased SNV |
|---|---|---|---|---|---|---|---|---|---|
| 1 | Comparison with CE and WGS/lobSTR | HGDP00932 | 696 (99.4%) | 290 | 406 | 58 | 86 | 144 | 159 |
|   |   | HGDP01414 | 687 (98.1%) | 288 | 399 | 45 | 89 | 134 | 155 |
|   |   | HGDP01032 | 695 (99.3%) | 322 | 373 | 65 | 83 | 148 | 174 |
|   |   | HGDP01034 | 691 (98.7%) | 292 | 399 | 50 | 84 | 134 | 159 |
|   |   | HGDP01035 | 691 (98.7%) | 301 | 390 | 57 | 76 | 133 | 158 |
|   |   | HGDP01417 | 695 (99.3%) | 315 | 380 | 56 | 76 | 132 | 162 |
|   |   | HGDP00457 | 694 (99.1%) | 305 | 389 | 50 | 106 | 156 | 182 |
|   |   | HGDP01028 | 693 (99.0%) | 310 | 383 | 50 | 82 | 132 | 152 |
|   |   | HGDP01030 | 692 (98.9%) | 283 | 409 | 55 | 100 | 155 | 173 |
|   | Trio validation | Child; PCR-free NC NA12878 | 686 (98.0%) | 326 | 360 | 46 | 70 | 116 | 132 |
|   |   | Father NA12891 | 692 (98.9%) | 312 | 380 | 48 | 76 | 124 | 144 |
|   |   | Mother NA12892 | 688 (98.3%) | 303 | 385 | 51 | 64 | 115 | 132 |
|   | PCR-free library | NA12878 | 688 (98.3%) | 333 | 355 | 54 | 74 | 128 | 147 |
|   | CRISPR/Cas9 fragmentation | Test NA12878 | 642 (91.7%) | 342 | 300 | 33 | 44 | 77 | 89 |
|   |   | Negative control | 625 (89.3%) | 323 | 302 | 25 | 40 | 65 | 75 |

TABLE 6-continued

STR-Seq Genotyping Summary

| Assay | Description | Sample | Genotyped STRs | Homozygous STR genotypes | Heterozygous STR genotypes | Homozygous STR-SNP haplotypes | Heterozygous STR-SNP haplotypes | Total phased STR | Total phased SNV |
|---|---|---|---|---|---|---|---|---|---|
| | Mixture analysis component | HGDP00924 | 636 (90.9%) | 306 | 330 | 32 | 53 | 85 | 101 |
| | | HGDP00925 | 664 (94.9%) | 285 | 379 | 44 | 56 | 100 | 115 |
| 2 | Trio validation | Child NA12878 | 1848 (78.0%) | 1,294 | 554 | 588 | 222 | 810 | 1,499 |
| | | Father NA12891 | 1863 (78.6%) | 1,308 | 555 | 600 | 235 | 835 | 1,604 |
| | | Mother NA12892 | 1854 (78.2%) | 1,256 | 598 | 592 | 249 | 841 | 1,608 |
| | Mixture analysis component | NA12891 | 1813 (76.5%) | 1252 | 561 | 505 | 185 | 690 | 1270 |
| | | NA12892 | 1756 (74.1%) | 1191 | 565 | 465 | 176 | 641 | 1136 |

Comparing the data from the amplification-free versus PCR-amplified libraries, the STR-containing reads with complete microsatellite sequences were examined. Overall, the median fraction of stutter decreased significantly from 3.2% to 0.9% (p<2.2e-16) (FIG. 12C). The amplification-free STR-Seq analysis identified homozygote alleles for six STRs that were called as heterozygotes using PCR-amplified libraries (Table 7). In these cases, stutter led to false heterozygotes allele calls.

TABLE 7

False Heterozygous Calls by PCR-amplified Library

| STR Identifier | Motif | PCR-free allele | PCR allele(s) |
|---|---|---|---|
| nc-SLC9A7 | T | 19 | 18, 19 |
| nc-ZNF302 | A | 30 | 29, 30 |
| NR-21_14 | A | 23 | 22, 23 |
| PentaC_9 | T | 35 | 35, 36 |
| trf420870_BAT26 | A | 26 | 25, 26 |
| trf604336_BAT25 | T | 39 | 38, 39 |

Example 6

CRISPR/Cas9 Targeted Fragmentation Improves Complete STR Read

Coverage

Figure 14:
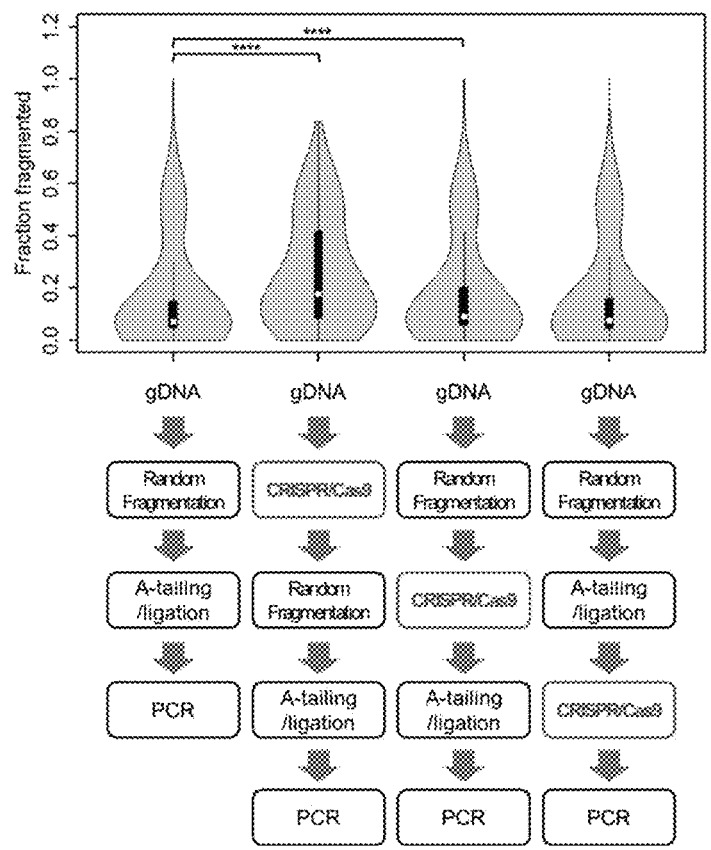
FIG. 14 shows the efficiency of targeted CRISPR/Cas9 fragmentation inserted between steps of sequencing library preparation. Bottom diagrams illustrate between which steps of the sequencing library process the targeted CRISPR/Cas9 fragmentation was inserted. Including the negative control, four sequencing libraries were made from HGDP00474, and sequenced using the Assay 1 probe pool. The distributions (top violin plots) are shown for fraction of sequencing reads of which the inserts start or stop at the site where gRNAs target. The median values are indicated as white dots inside the black boxes. The horizontal thickness represents estimated Kernel density, and the significance is indicated at the top of plots.

As a solution for truncated microsatellite sequences resulting from random DNA fragmentation, an in vitro CRISPR/Cas9 targeted fragmentation process was developed. As an initial step prior to library preparation, the gRNAs bind to the complementary DNA target site and in combination with Cas9, produce a blunt-ended, double-strand break (FIG. 14; Table 1).

Figure 15:
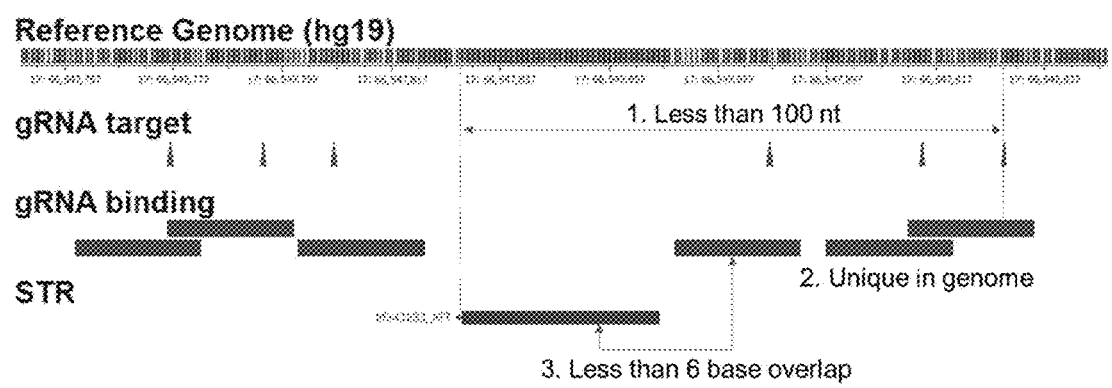
FIG. 15 shows an embodiment of the design criteria for gRNA. A set of gRNAs were designed to target upstream and downstream of STR loci. Three criteria were used to select the gRNA target sequences: i) the break site is located such that a sequencing read starting from the break would include the entire repeat within a 100-base read length; ii) the binding sequence should be uniquely represented in the human genome; and iii) the binding sequence should not overlap more than 6 bp with the STR repeat. Overall, 8,348 gRNAs targeting 2,104 repeat regions were identified.

A set of gRNAs were designed to fragment DNA either upstream or downstream of the STRs targeted by Assays 1 and 2. Three criteria were used to select the gRNA target sequences (FIG. 15): i) the fragmentation site included the entire repeat within a 100-base read length; ii) the binding region sequence was uniquely represented in the human genome; and iii) the gRNA sequence did not overlap more than 6 bp with the STR repeat. Overall, 8,343 gRNAs targeting 2,103 repeat regions were identified. The gRNA reagents were generated with array-synthesized oligonucleotides incorporating a T7 promoter (see, Materials and Methods). The oligonucleotides were amplified and gRNA was produced in vitro. Genomic DNA was treated with the CRISPR/Cas9 enzyme and the synthesized gRNAs.

Figure 16:
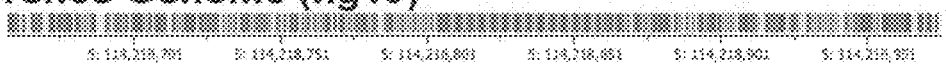
FIG. 16 shows the performance of targeted CRISPR/Cas9 fragmentation. 16A: For the STR target presented here (trf676281; [ATAG]n), two gRNAs were designed with two pairs of primer probes. Read depth and pile-up of Read is are compared between negative control and target-specifically fragmented sample DNAs. In the pile-up plots, Read is from plus probes (binding downstream of the STR) align to the reference itself (forward reads; blue) while those from minus probe align to the reverse complementary of reference (reverse reads; green). For the CRISPR/Cas9 targeted fragmentation, 92% and 67% among all reads having an overlap with 2 base-upstream or downstream of the break position started or stopped at the break (indicated by red dotted arrows). Read depth for the STR region (shaded) was higher than that of other flanking regions when the targeted fragmentation was used. In the reference genome, red, yellow, green, and blue bars indicate A, C, G, and T bases, respectively. 16B: The read distribution for CRISPR/Cas9 target sites are shown that start or stop within 2 bp of the target cut site. The median values are indicated as white dots inside the black boxes. The horizontal thickness represents estimated and normalized Kernel density. 16C: Estimated Kernel density for observed frequency allele fraction of heterozygous alleles is separately shown for STRs with and without gRNA targeting. The distribution is significantly different between negative control and test runs for gRNA-targeted STRs (top), but similar for non gRNA-targeted STRs (bottom).
Figure 16:
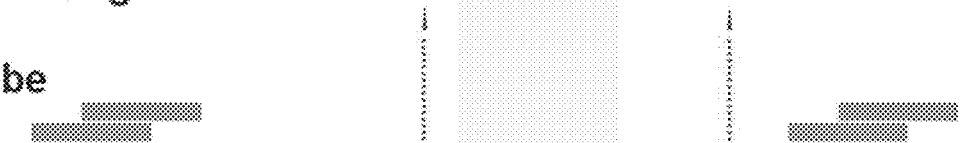
Figure 16:
Figure 16:
Figure 16:
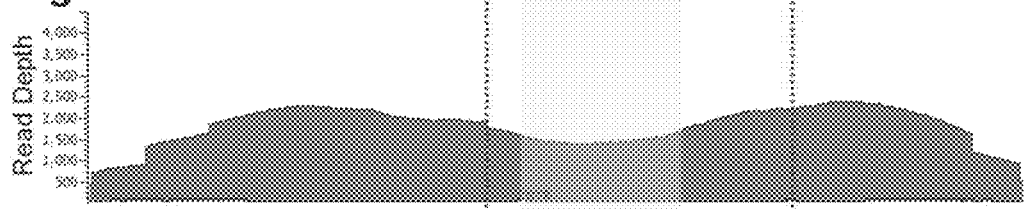
Figure 16:
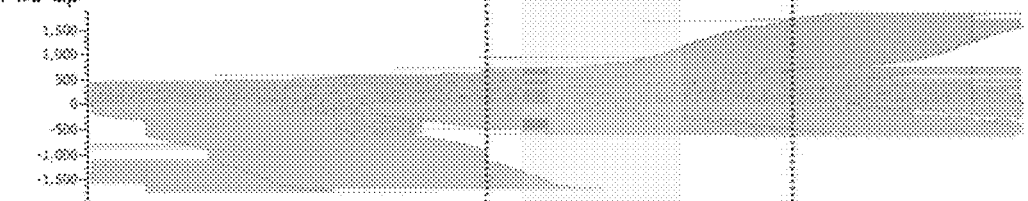
Figure 16:
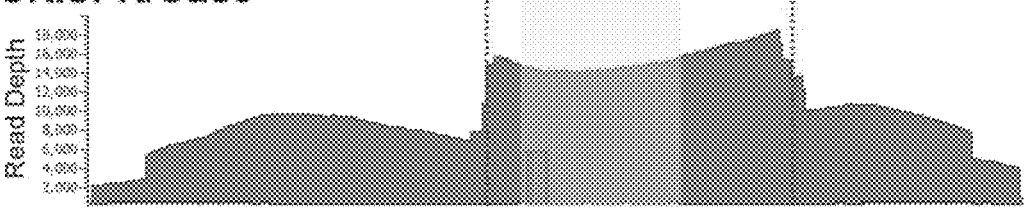
Figure 16:
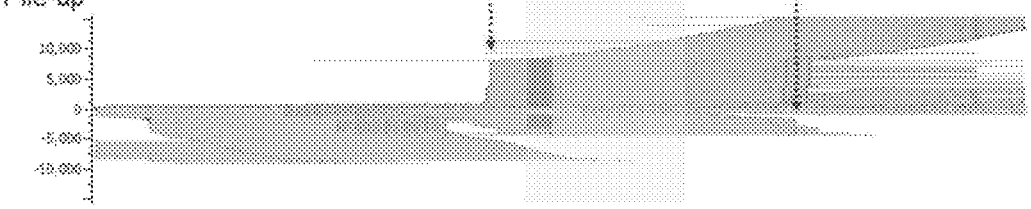
Figure 16:
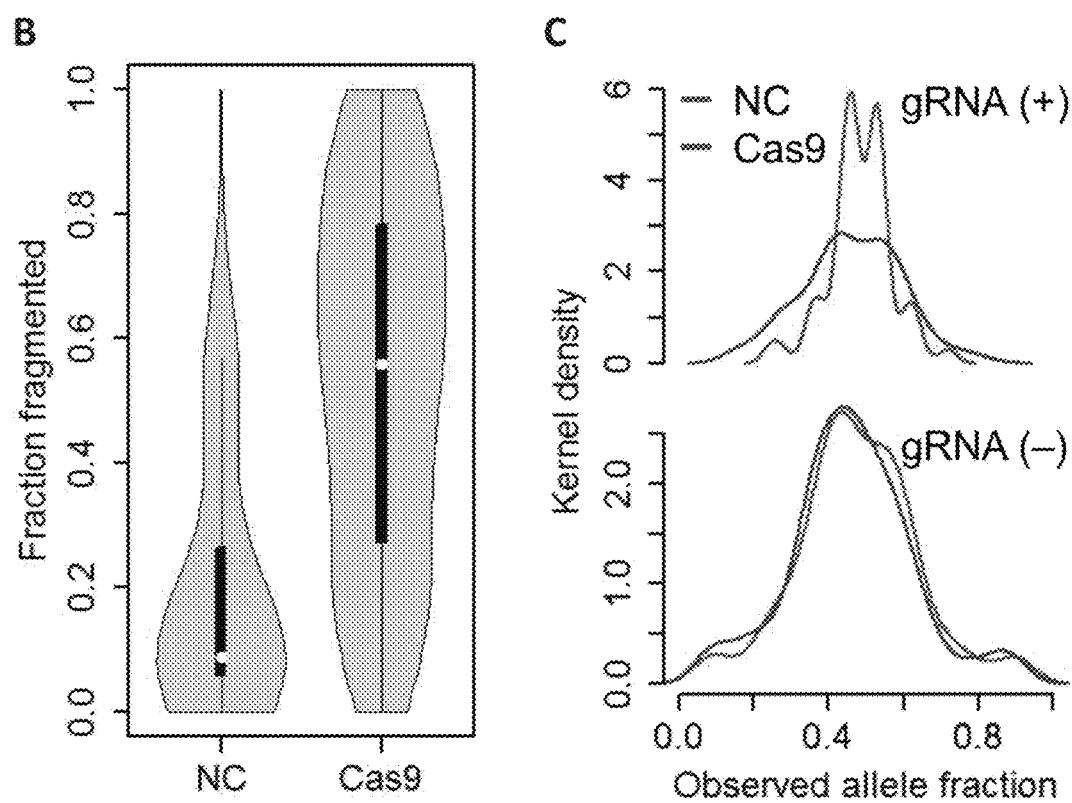
Figure 17:
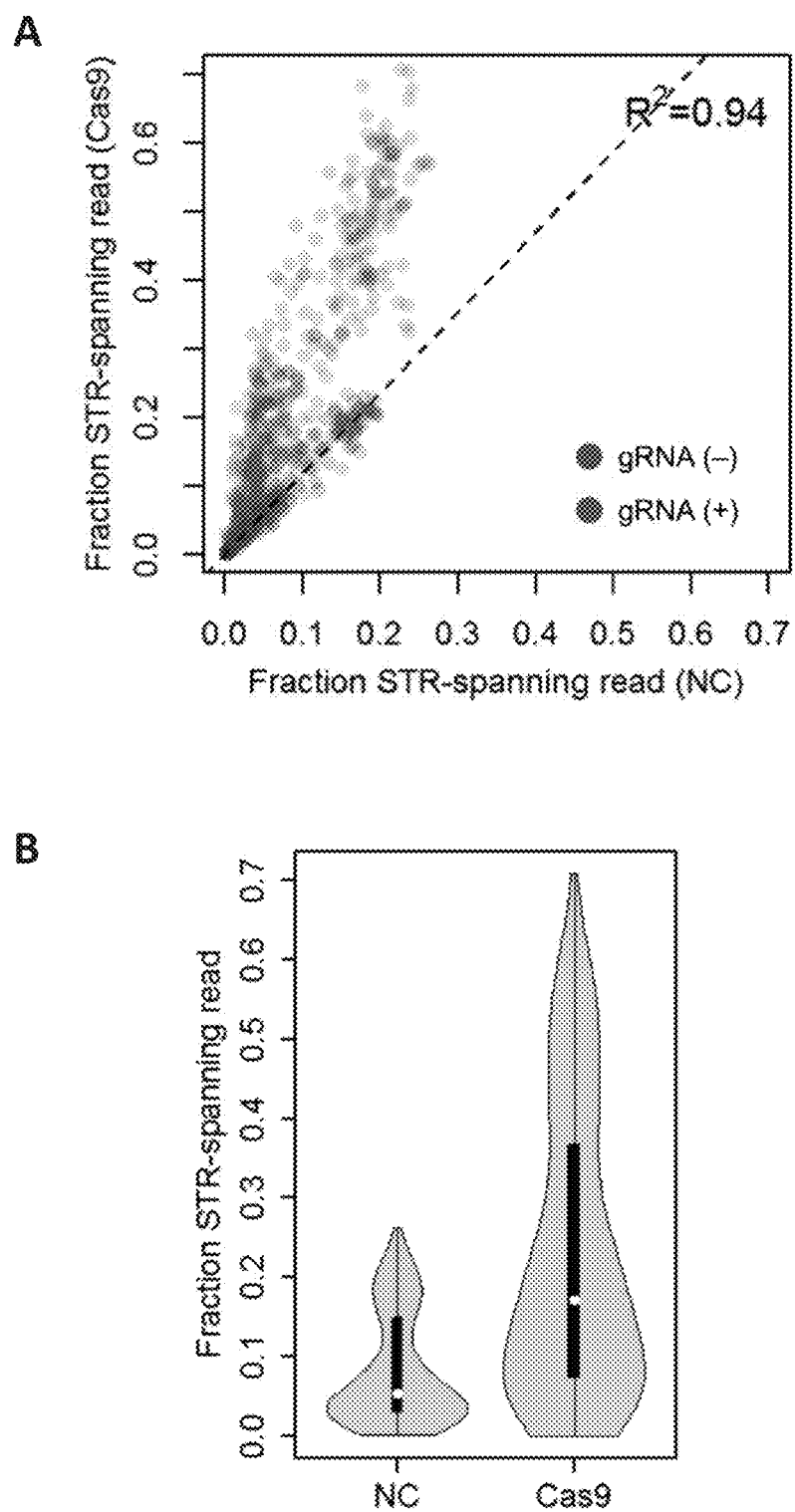
FIG. 17 shows the effect of targeted CRISPR/Cas9 fragmentation on fraction of STR-spanning read. 17A: Fraction of STR spanning read for each STR target is plotted for both negative control (x-axis) and target-specifically fragmented (y-axis) samples. Among 599 STR targets having matching genotype call from both samples, 474 targets were targeted by gRNA (blue) and remaining 125 had no gRNA targeting (red). For non-targeted STRs, R-squared value is indicated with regression line to show the fraction is reproducible when an STR is not targeted by gRNA. 17B: Estimated Kernel density is shown for both negative control and target-specifically fragmented samples. The distributions include only the STRs targeted by gRNAs which is plotted as red circles in FIG. 17A. The median values are indicated as white dots inside the black boxes.

After targeted fragmentation, NA12878 was analyzed with Assay 1. After sequencing, the exact position of the fragment's cleavage site was determined from Read 1 (FIG. 16A). Sequence reads in which the flanking sequence was within 4 bases of the expected gRNA fragmentation position were classified as being on-targeted and counted. Overall, 56% of the reads showed the specific CRISPR fragment position compared to random fragmentation that showed 8.7% (FIG. 16B). Compared to random fragmentation, the CRISPR/Cas9 procedure showed a significant increase (p<2.2e-16) in the fraction of STR-spanning reads. Furthermore, a three-fold increase (from 5.3% to 17.1%) in the median STR-spanning read fraction was observed (FIGS. 17A-17B).

From the analysis with Assay 1, 642 STR genotypes were identified with CRISPR targeted fragmentation compared to 625 STR genotypes with random fragmentation (Table 6). The allelic fraction of each STR genotype as measured by counting reads with one genotype versus the other was examined (FIG. 16C). Assuming the sequencing assay perfectly reflects the variants in a diploid sample, for a heterozygote STR allele 50% of the reads would be observed, a direct reflection of the allele fraction, having one genotype and the remaining 50% having the other. Without CRISPR targeting, a wide distribution of allele fractions (standard deviation=0.13) was observed across the heterozygous STRs. With CRISPR targeting, the distribution of allelic fractions (standard deviation=0.08) was smaller. This result confirms that CRISPR improves the quantitative assessment of allelic fraction with better precision.

Example 7

Haplotypes Distinguish the Minor Fraction Components in DNA Mixtures

STR-Seq's sensitivity in detecting a specific genomic DNA sample among a series of DNA mixture (Table 8) was evaluated by combining samples in varying ratios.

TABLE 8

Results of the STR-Seq Haplotype Analysis of Genetic Mixtures

| Assay Sample | | Description | | Number informative haplotype | Median coverage for informative loci |
|---|---|---|---|---|---|
| 1 | HGDP00924 (minor) + HGDP00925 | 2-component mixture | 25.0% | 25 | 153 |
| | | | 10.0% | 23 | 137 |
| | | | 5.0% | 23 | 160 |
| | | | 1.0% | 21 | 798 |
| | | | 0.5% | 19 | 1,206 |
| | | | 0.1% | 11 | 1,332 |
| | HGDP00924 (minor) + 5 HGDP samples | 6-component mixture | 25.0% | 16 | 135 |
| | | | 10.0% | 13 | 102 |
| | | | 5.0% | 15 | 215 |
| | | | 1.0% | 16 | 868 |
| | | | 0.5% | 13 | 917 |
| | | | 0.1% | 5 | 1,908 |
| 2 | NA12892 (minor) + NA12891 | 2-component mixture | 40.0% | 71 | 34 |
| | | | 20.0% | 66 | 48 |
| | | | 5.0% | 47 | 52 |
| | | | 1.0% | 12 | 46 |

1) Median coverage: median of number of read pairs having a full span of the STR region (Read 1) and a base call at the SNV site (Read 2)

Figure 18:
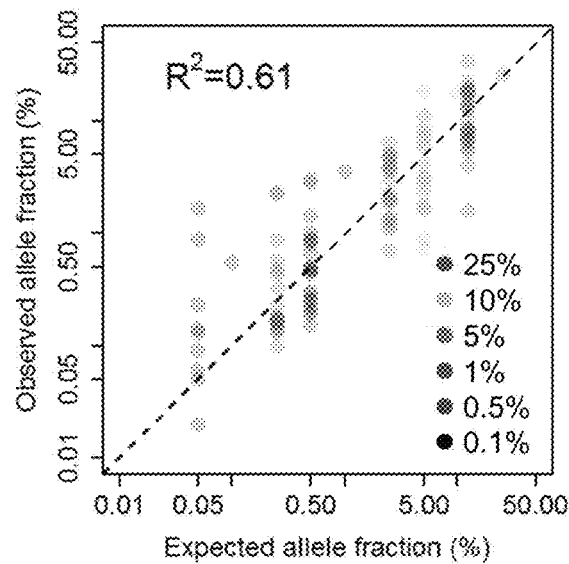
FIG. 18 shows the sensitive detection of minor component's haplotype in mixture DNA. 18A: Observed allele fractions of informative haplotypes are plotted against expected ratio based on the minor component fractions (25% to 0.1%) of a 2-component mixture (HGDP00924 as minor and HGDP00925 as major). The scale of both x- and y-axes are shown in log scale. The R-squared value is shown at the top left in the plot, and the dotted diagonal line indicates 1:1 concordance. 18B: A mixture of two individuals (0.1% HGDP00924 and 99.9% HGDP00925) was analyzed for a dinucleotide repeat (trf291274). M and N alleles indicate genotypes from the major and minor components, respectively. The bar graph in the right box shows read counts for all observed alleles separately for two SNP alleles found by STR-Seq analysis. A haplotype (11 motif repeats and G allele) specific to minor component was detectable. On the other hand, the bar graph on the bottom left shows collective read counts regardless of linked SNP genotype. Both alleles from minor components are not detectable because they are mixed with artificial indels from the major component.
Figure 18:
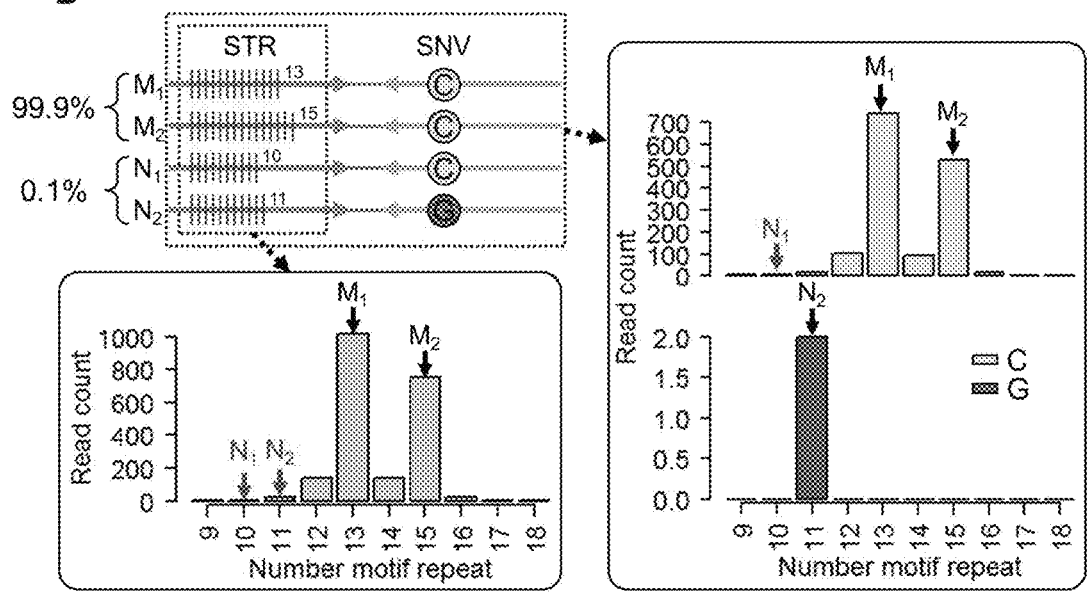

Two unrelated DNA samples (HGDP00924 and HGDP00925) were used where HGDP00924 represented the minor component of the mixture. DNA from HGDP00924 was added in decreasing ratios from 25% to 0.1%. First, haplotypes for the two samples were determined individually. With Assay 1, STR-Seq was used to analyze HGDP00924 alone and haplotypes were compared to HGDP00925. 29 unique haplotypes present in HGDP00924 and not present in HGDP00925 were identified. These 29 haplotypes were evaluated and determined if read counting provided an accurate quantitative measurement of the minor component contribution to the mixture. Overall, the HGDP00924 fraction as observed by the sequence reads showed a strong correlation with the known mixture ratio (FIG. 18A; $R^2$=0.61, p<2.2e-16). Even with the minor component ratio of 0.1%, 11 of the HGDP00924 haplotypes were detected (Table 8).

Figure 19:
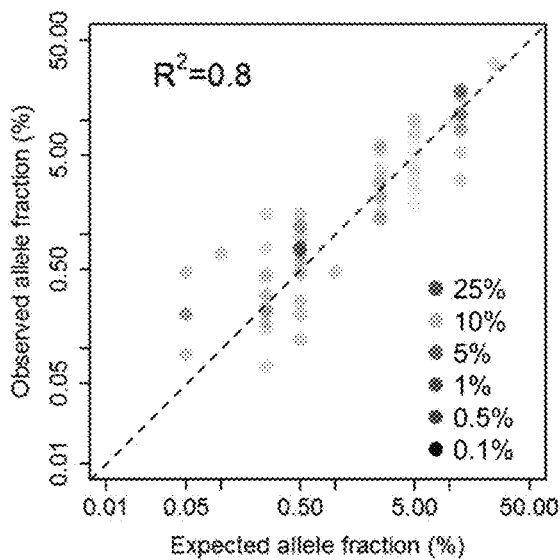
FIG. 19 shows the observed allele fraction of informative haplotype in mixture analysis. Observed allele fractions of informative haplotypes are plotted against expected fractions based on minor component ratio for 6-component mixtures (19A; HGDP00924 as minor and equimolar mixture of 5 other HGDP samples as major) and 2-component mixtures (19B; NA12892 as minor and NA12891 as major). The scale of both x- and y-axes are shown in log scale. The R-squared value is shown at the top left in the plot, and the dotted line indicates the diagonal.
Figure 19:
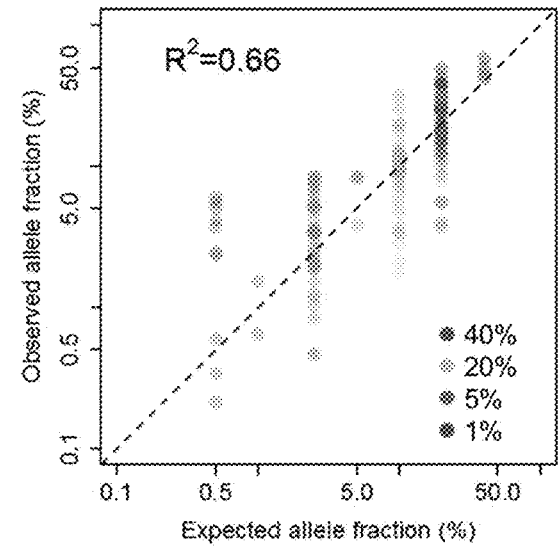

For the next experiment, a six-component mixture was generated. Five DNA samples from unrelated individuals were combined in equimolar ratio and then a minor component DNA (HGDP00924) was added in decreasing ratios ranging from 25% to 0.1%. For HGDP00924's 29 STR-SNP haplotypes, 16 demonstrated a decreasing fraction that correlated with expected mixture ratio. This result suggested that these 16 haplotypes were unique to HGDP00924 compared to the five other samples (FIG. 19A). Five of the HGDP00924-informative haplotypes were still detectable even at a ratio of 0.1% (Table 8).

For additional validation, a different two-component mixture (NA12892 and NA12891) was generated. Mixture ratios ranged from a 40% to 1% fraction with NA12892 being the minor component. This STR-Seq analysis was conducted with both CRISPR targeted fragmentation and PCR-free library preparation. Using Assay 2, the two sample DNAs were analyzed separately, and 122 haplotypes unique to NA12892 were identified. These haplotypes demonstrated an allelic fraction that was highly correlated with the minor component ratio (FIG. 19B; $R^2$=0.66, p<2.2e-16). It was observed that the goodness-of-fit value ($R^2$) improved with CRISPR targeted fragmentation.

For the 1% fraction, STR-Seq called 12 haplotypes specific to the NA12892 minor component. Four informative loci had coverage greater than 150, and the allele fraction of these haplotype-specific reads matched the mixture ratio (i.e. approximately 0.5% or 1% for each haplotype per each locus depending on zygosity). The remaining eight haplotypes had lower coverage with less precision in their allelic fraction at 1.5% or greater (Table 9). Higher coverage sequencing will further improve the precision of this analysis.

TABLE 9

Minor Component Specific Haplotypes Detected in a 2-Component Mixture (99% NA12891 and 1% NA12892)

| SNP position | STR name | Coverage | Minor component-specific haplotype | Fraction of haplotype-specific reads |
|---|---|---|---|---|
| 8:3433876 | trf804202 | 1185 | C-12 | 0.34% |
| 3:64526610 | trf548074 | 481 | G-3.57 | 0.21% |
| 8:4365670 | trf804571 | 170 | A-2.26 | 0.59% |
| 13:101941919 | trf226617 | 157 | T-10 | 0.64% |
| 8:72930436 | trf825340 | 66 | A-7 | 1.52% |
| 12:17880216 | trf164062 | 48 | T-3.5 | 4.17% |
| 4:162232005 | trf633419 | 43 | T-10 | 2.33% |
| 4:162231931 | trf633419 | 41 | T-10 | 2.44% |
| 12:17880297 | trf164062 | 33 | C-3.5 | 6.06% |
| 2:34454506 | trf416876 | 27 | A-16 | 3.70% |
| 6:22311719 | trf703632 | 20 | G-18 | 5.00% |
| 13:22819829 | trf203882 | 18 | C-8 | 5.56% |

1) Coverage: number of read pairs having a full span of the SIR region (Read 1) and a base call at the SNP site (Read 2)

The invention claimed is:

1. A method for analyzing short tandem repeats (STRs), comprising:
   (a) separately digesting, using an RNA-guided nuclease:
      (i) a first portion of a genomic sample from an individual, at a defined site that is upstream of an STR; and
      (ii) a second portion of the sample, at a defined site that is downstream of the STR, to produce first and second digestion products;
   (b) fragmenting the first and second digestion products of step (a) to produce first and second fragmentation products;
   (c) ligating an adaptor to the fragmentation products of step (b) to produce first and second ligation products;
   (d) selectively amplifying, using strand-specific primers and a primer that hybridizes to the adaptor:
      (i) part of the top strand but not the bottom strand of the first ligation products; and
      (ii) part of the bottom strand but not the top strand of the second ligation products;
   (e) sequencing at least some of the amplification products of step (d) to produce a plurality of top strand reads and a plurality of bottom strand reads; and
   (f) counting the number of STR repeats in a sequence read of step (e), thereby providing an allele-specific count of the number of STR repeats at a particular locus in the genome of the individual.

2. The method of claim 1, wherein the sequencing step (e) is paired-end sequencing, and wherein the method comprises, prior to said counting step (f), eliminating sequence reads that do not contain the sequence of a primer used in step (d).

3. The method of claim 1, further comprising validating the number of STR repeats counted in (f) as being accurate only if the number matches the number of STR repeats counted in a read from the other strand.

4. The method of claim 1, wherein the sequencing step (e) is paired-end sequencing, and wherein the method comprises analyzing the paired-end read to determine the allele of a sequence variation that is linked to the STR.

5. The method of claim 1, wherein step (d) is done on a solid support.

6. The method of claim 1, wherein step (d) is done in solution.

7. The method of claim 1, wherein the method comprises pooling the products of step (a), (b), (c) or (d).

8. The method of claim 1, further comprising analyzing the numbers of STR repeats in further sequence reads of step (e).

9. The method of claim 8, wherein the numbers of STR repeats in the further sequence reads are validated as being accurate only if the further sequence reads match sequence reads from the other strand.

10. The method of claim 8, further comprising determining whether the individual is homozygous for a particular allele of the STR.

11. The method of claim 8, further comprising determining whether the individual is heterozygous for different alleles of the STR.

12. The method of claim 1, wherein the method comprises analyzing a plurality of STRs, thereby producing an STR fingerprint.

13. The method of claim 12, further comprising comparing the STR fingerprint to an STR fingerprint from a second individual to determine if the individuals are related.

14. The method of claim 12, further comprising comparing the STR fingerprint to an STR fingerprint obtained from a sample obtained from a crime scene.

15. The method of claim 12, wherein the genomic sample is from a cancer biopsy.

16. The method of claim 15, further comprising comparing the STR fingerprint for the cancer biopsy to an STR fingerprint for a second cancer biopsy, to provide a clonal analysis of cancer progression.

* * * * *

SEQUENCE LISTING

<160> NUMBER OF SEQ ID NOS: 8

<210> SEQ ID NO 1
<211> LENGTH: 23
<212> TYPE: DNA
<213> ORGANISM: Artificial sequence
<220> FEATURE:
<223> OTHER INFORMATION: Synthetic nucleotide sequence.
<220> FEATURE:
<221> NAME/KEY: misc_feature
<222> LOCATION: (1)..(7)
<223> OTHER INFORMATION: There may be phosphorothioate bonding between
      each of the nucleotides 1 to 7.

<400> SEQUENCE: 1
aatgatacgg cgacggatca agu                                           23

<210> SEQ ID NO 2
<211> LENGTH: 24
<212> TYPE: DNA
<213> ORGANISM: Artificial sequence
<220> FEATURE:
<223> OTHER INFORMATION: Synthetic nucleotide sequence.
<220> FEATURE:
<221> NAME/KEY: misc_feature
<222> LOCATION: (1)..(1)
<223> OTHER INFORMATION: This nucleotide may have a 5' phosphate.

<400> SEQUENCE: 2
caagcagaag acggcatacg agat                                          24

<210> SEQ ID NO 3
<211> LENGTH: 20
<212> TYPE: DNA
<213> ORGANISM: Artificial sequence
<220> FEATURE:
<223> OTHER INFORMATION: Synthetic nucleotide sequence.

<400> SEQUENCE: 3
gagcttcggt tcacgcaatg                                               20

<210> SEQ ID NO 4
<211> LENGTH: 79
<212> TYPE: DNA
<213> ORGANISM: Artificial sequence
<220> FEATURE:
<223> OTHER INFORMATION: Synthetic nucleotide sequence.

<400> SEQUENCE: 4
aaagcaccga ctcggtgcca cttttcaag ttgataacgg actagcctta ttttaacttg    60
ctatttctag ctctaaaac                                                79

<210> SEQ ID NO 5
<211> LENGTH: 41
<212> TYPE: DNA
<213> ORGANISM: Artificial sequence
<220> FEATURE:
<223> OTHER INFORMATION: Synthetic nucleotide sequence.
<220> FEATURE:
<221> NAME/KEY: misc_feature
<222> LOCATION: (40)..(41)
<223> OTHER INFORMATION: There may be a phosphorotioate bond between
      nucleotides 40 and 41.

<400> SEQUENCE: 5
cgagatctac actctttccc tacacgacgc tcttccgatc t                       41

```
<210> SEQ ID NO 6
<211> LENGTH: 40
<212> TYPE: DNA
<213> ORGANISM: Artificial sequence
<220> FEATURE:
<223> OTHER INFORMATION: Synthetic nucleotide sequence.
<220> FEATURE:
<221> NAME/KEY: misc_feature
<222> LOCATION: (1)..(1)
<223> OTHER INFORMATION: This nucleotide may have a 5' phosphate.

<400> SEQUENCE: 6
gatcggaaga gcgtcgtgta gggaaagagt gtagatctcg                          40

<210> SEQ ID NO 7
<211> LENGTH: 48
<212> TYPE: DNA
<213> ORGANISM: Artificial sequence
<220> FEATURE:
<223> OTHER INFORMATION: Synthetic nucleotide sequence.
<220> FEATURE:
<221> NAME/KEY: misc_feature
<222> LOCATION: (42)..(47)
<223> OTHER INFORMATION: Nucleotides 42 to 47 may be any nucleotide.
<220> FEATURE:
<221> NAME/KEY: misc_feature
<222> LOCATION: (47)..(48)
<223> OTHER INFORMATION: There may be a phosphorothioate bond between
      nucleotides 47 and 48.

<400> SEQUENCE: 7
cgagatctac actctttccc tacacgacgc tcttccgatc tnnnnnnt                 48

<210> SEQ ID NO 8
<211> LENGTH: 47
<212> TYPE: DNA
<213> ORGANISM: Artificial sequence
<220> FEATURE:
<223> OTHER INFORMATION: Synthetic nucleotide sequence.
<220> FEATURE:
<221> NAME/KEY: misc_feature
<222> LOCATION: (1)..(6)
<223> OTHER INFORMATION: Nucleotides 1 to 6 may be any nucleotide.
<220> FEATURE:
<221> NAME/KEY: misc_feature
<222> LOCATION: (1)..(1)
<223> OTHER INFORMATION: This nucleotide may have a 5' phosphate.

<400> SEQUENCE: 8
nnnnnnagat cggaagagcg tcgtgtaggg aaagagtgta gatctcg                  47
```